(12) United States Patent
Yoon et al.

(10) Patent No.: US 10,545,050 B2
(45) Date of Patent: Jan. 28, 2020

(54) OPTICAL SIGNAL PROCESSING METHOD AND APPARATUS

(71) Applicant: SAMSUNG ELECTRONICS CO., LTD., Suwon-si (KR)

(72) Inventors: Youngzoon Yoon, Hwaseong-si (KR); Hyochul Kim, Yongin-si (KR); Younggeun Roh, Seoul (KR)

(73) Assignee: SAMSUNG ELECTRONICS CO., LTD., Suwon-si (KR)

( * ) Notice: Subject to any disclaimer, the term of this patent is extended or adjusted under 35 U.S.C. 154(b) by 0 days.

(21) Appl. No.: 16/181,783

(22) Filed: Nov. 6, 2018

(65) Prior Publication Data

US 2019/0154503 A1     May 23, 2019

(30) Foreign Application Priority Data

Nov. 23, 2017   (KR) .................. 10-2017-0157508

(51) Int. Cl.
*G01J 3/28*     (2006.01)
*G01J 3/26*     (2006.01)
*G01J 3/10*     (2006.01)

(52) U.S. Cl.
CPC ............. *G01J 3/2803* (2013.01); *G01J 3/10* (2013.01); *G01J 3/26* (2013.01); *G01J 2003/2873* (2013.01)

(58) Field of Classification Search
CPC .... G01J 3/2803; G01J 3/10; G01J 3/26; G01J 2003/2873; A61B 5/1455; A61B 5/0075; A61B 5/7221; A61B 5/203; A61B 2562/185; A61B 5/6832; A61B 2562/0233; A61B 2562/046
See application file for complete search history.

(56) References Cited

U.S. PATENT DOCUMENTS

| | | | | |
|---|---|---|---|---|
| 4,002,899 A | * | 1/1977 | Stauffer | G02B 7/30 250/201.8 |
| 7,605,918 B2 | | 10/2009 | Darlrymple | |
| 8,159,668 B2 | | 4/2012 | Malinen et al. | |
| 9,885,607 B2 | | 2/2018 | Eom | |
| 2010/0103300 A1 | * | 4/2010 | Jones | H04N 5/3415 348/302 |

(Continued)

FOREIGN PATENT DOCUMENTS

| | | |
|---|---|---|
| EP | 2656774 A1 | 10/2013 |
| KR | 10-2010-0063112 A | 6/2010 |

(Continued)

OTHER PUBLICATIONS

Communication dated Feb. 27, 2019, issued by the European Patent Office in counterpart European Application No. 18206935.1.

(Continued)

*Primary Examiner* — Abdullahi Nur
(74) *Attorney, Agent, or Firm* — Sughrue Mion, PLLC

(57) ABSTRACT

An optical signal processing apparatus may acquire a plurality of image signals using an optical signal output from a light source toward a target, and may determine a characteristic of a target by using the obtained plurality of image signals. The obtained image signal may be obtained from a plurality of sensor arrays including a plurality of image sensors.

21 Claims, 21 Drawing Sheets

(56) References Cited

U.S. PATENT DOCUMENTS

| | | | |
|---|---|---|---|
| 2014/0160326 A1* | 6/2014 | Black | H04N 5/2257 |
| | | | 348/262 |
| 2016/0110844 A1* | 4/2016 | Humfeld | H04N 5/23232 |
| | | | 348/239 |
| 2016/0258884 A1* | 9/2016 | Kang | G01N 23/04 |
| 2016/0290864 A1 | 10/2016 | Roy et al. | |
| 2018/0260649 A1* | 9/2018 | Kadambe | G06K 9/3241 |
| 2019/0101444 A1 | 4/2019 | Yoon et al. | |

FOREIGN PATENT DOCUMENTS

| | | | |
|---|---|---|---|
| KR | 10-2017-0023628 A | | 3/2017 |
| KR | 10-2019-0038177 A | | 4/2019 |
| WO | 2017025775 A1 | | 2/2017 |

OTHER PUBLICATIONS

Jie Bao et al. "A colloidal quantum dot spectrometer" Letter, vol. 523, Nature, Jul. 2, 2015, 16 pages total.

Cheng-Chun Chang et al. "On the estimation of target spectrum for filter-array based spectrometers" Optics Express, vol. 16, No. 2, Jan. 21, 2008, (pp. 1056-1061).

* cited by examiner

Reference Calibration by metal black box

FIG. 14
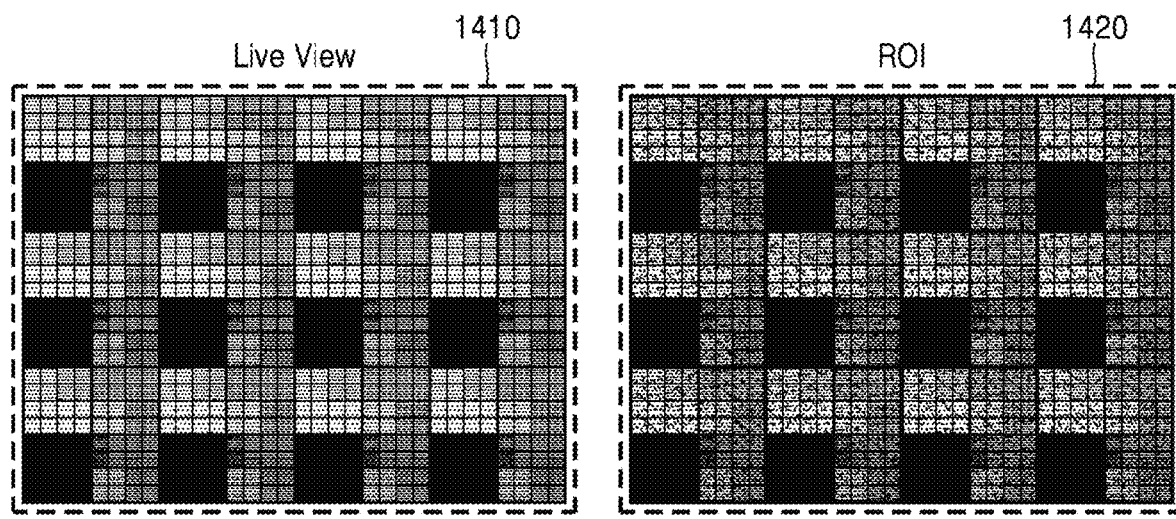
Non uniform inlet light Effect A
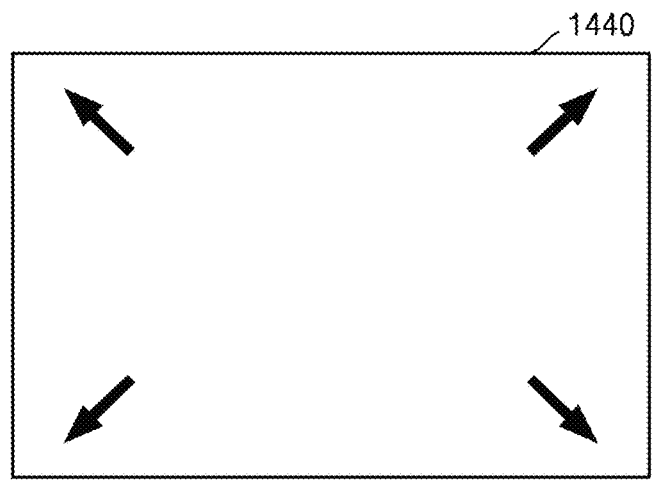
Inlet light distribution A

OPTICAL SIGNAL PROCESSING METHOD AND APPARATUS

RELATED APPLICATION

This application claims priority from Korean Patent Application No. 10-2017-0157508, filed on Nov. 23, 2017 in the Korean Intellectual Property Office, the disclosure of which is incorporated herein by reference in its entirety.

BACKGROUND

1. Field

Apparatuses and methods consistent with exemplary embodiments relate to detecting and measuring an optical signal using a plurality of sensor arrays.

2. Description of the Related Art

An optical signal processing apparatus, such as a spectrometer, may determine characteristics of a target by outputting an optical signal to the target and detecting light scattered or reflected from the target. For example, the optical signal processing apparatus may perform a body component analysis, and/or measure various chemical and physiological states of a living body. In particular, the optical signal processing apparatus may measure a physiological state such as blood sugar or cholesterol, and/or measure a state of food in a refrigerator. There is an increasing demand for an optical signal processing apparatus capable of more precisely determining a characteristic of a target.

SUMMARY

One or more exemplary embodiments provide optical signal processing apparatuses for determining a characteristic of a target by using a plurality of sensor arrays.

According to an aspect of an exemplary embodiment, there is provided an apparatus for processing an optical signal, the apparatus including: a light source configured to output a light; a first sensor array including a plurality of first image sensors configured to obtain a first image signal by detecting the light scattered, reflected, or refracted from a target; a second sensor array disposed in an area adjacent to the first sensor array, and including a plurality of second image sensors configured to obtain a second image signal having repeatability with the first image signal by detecting the light scattered, reflected, or refracted from the target; and a processor configured to determine a characteristic of the target based on an analysis result of the first image signal and the second image signal.

A number of the plurality of first image sensors included in the first sensor array and a number of the plurality of second image sensors included in the second sensor array may be predetermined unit numbers.

The processor may be further configured to update an operation method of at least one of the light source, the first sensor array, and the second sensor array, according to the analysis result.

The processor may be further configured to control the light source to adjust at least one of an intensity of the light outputted from the light source and an output angle of the light outputted from the light source, according to the analysis result.

The processor may be further configured to adjust an exposure time of at least one of the first sensor array and the second sensor array, according to the analysis result.

The analysis result may include a signal to noise ratio (SNR) of the first image signal or the second image signal, wherein the processor may be further configured to adjust an operation method of at least one of the light source, the first sensor array, and the second sensor array according to the SNR when the SNR is less than a predetermined value.

The analysis result may include a saturation degree of the first image signal or the second image signal, wherein the processor may be further configured to adjust an exposure time of at least one of the first sensor array and the second sensor array according to the saturation degree when the saturation degree is greater than or equal to a predetermined value.

The processor may be further configured to determine the characteristic of the target by using one of the first image signal and the second image signal according to the analysis result.

The processor may be further configured to obtain the analysis result by comparing the first image signal to the second image signal based on a position of a first reference sensor which is one of the plurality of first image sensors and a position of a second reference sensor which is one of the second plurality of image sensors.

The processor may be further configured to determine offsets of the first image signal and the second image signal by using a signal obtained from the first reference sensor and a signal obtained from the second reference sensor.

According to an aspect of another exemplary embodiment, there is provided a method of processing an optical signal, the method including: outputting a light; obtaining a first image signal by detecting the light scattered, reflected, or refracted from a target by using a first sensor array including a plurality of first image sensors; obtaining a second image signal having repeatability with the first image signal by detecting the light scattered, reflected, or refracted from the target by using a second sensor array that is disposed in an area adjacent to the first sensor array and includes a plurality of second image sensors; and determining a characteristic of the target based on an analysis result of the first image signal and the second image signal.

A number of the plurality of first image sensors included in the first sensor array and a number of the plurality of second image sensors included in the second sensor array may be predetermined unit numbers.

The method may further include adjusting at least one of an operation method of outputting the light, an operation method of obtaining the first image signal, and an operation method of obtaining the second image signal, according to the analysis result.

The method may further include: adjusting at least one of an intensity of the outputted light and an output angle of the outputted light according to the analysis result.

The method may further include: adjusting an exposure time of at least one of the first sensor array and the second sensor array, according to the analysis result.

The analysis result may include a signal to noise ratio (SNR) of the first image signal or the second image signal; and the method may further include: adjusting at least one of an operation method of outputting the light, an operation method of obtaining the first image signal, and an operation method of obtaining the second image signal, according to the SNR when the SNR is less than a predetermined value.

The analysis result may include a saturation degree of the first image signal or the second image signal; and the method may further include adjusting an exposure time of at least one of the first sensor array and the second sensor array, according to the saturation degree when the saturation degree is greater than or equal to a predetermined value.

The method may further include: determining the characteristic of the target by using one of the first image signal and the second image signal according to the analysis result.

The method may further include: obtaining the analysis result by comparing the first image signal to the second image signal based on a position of a first reference sensor which is one of the plurality of first image sensors and a position of a second reference sensor which is one of the plurality of second image sensors.

The method may further include: determining offsets of the first image signal and the second image signal by using a signal obtained from the first reference sensor and a signal obtained from the second reference sensor.

According to an aspect of another exemplary embodiment, there is provided a non-transitory computer-readable storage medium storing a program that is executable by a computer to perform the method of processing an optical signal.

BRIEF DESCRIPTION OF THE DRAWINGS

The above and/or other aspects will be more apparent by describing certain exemplary embodiments, with reference to the accompanying drawings, in which:

FIG. 14 is a diagram illustrating an example in which an optical signal processing apparatus according to an exemplary embodiment analyzes an image signal when light is relatively uniformly distributed;

DETAILED DESCRIPTION

Figure 1:
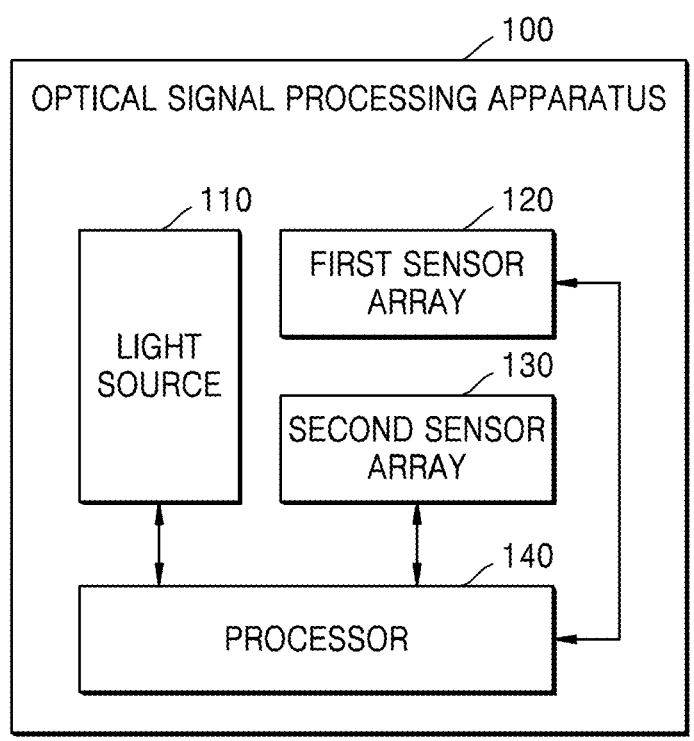
FIG. 1 is a block diagram showing a configuration of an optical signal processing apparatus according to an exemplary embodiment.

Exemplary embodiments are described in greater detail below with reference to the accompanying drawings.

In the following description, like drawing reference numerals are used for like elements, even in different drawings. The matters defined in the description, such as detailed construction and elements, are provided to assist in a comprehensive understanding of the exemplary embodiments. However, it is apparent that the exemplary embodiments can be practiced without those specifically defined matters. Also, well-known functions or constructions are not described in detail since they would obscure the description with unnecessary detail.

First, the terms used in the present disclosure will be briefly described below before exemplary embodiments of the present disclosure are described in greater detail.

Most of the terms used herein are general terms that have been widely used in the technical art to which the present disclosure pertains. However, some of the terms used herein may be created reflecting intentions of technicians in this art, precedents, or new technologies. Also, some of the terms used herein may be arbitrarily chosen by the present applicant. In this case, these terms are defined in detail below. Accordingly, the specific terms used herein should be understood based on the unique meanings thereof and the whole context of the present disclosure.

Throughout the specification, when a portion "includes" an element, another element may be further included, rather than excluding the existence of the other element, unless otherwise described.

Expressions such as "at least one of," when preceding a list of elements, modify the entire list of elements and do not modify the individual elements of the list. For example, the expression, "at least one of a, b, and c," should be understood as including only a, only b, only c, both a and b, both a and c, both b and c, or all of a, b, and c.

An optical signal processing apparatus 100 according to an exemplary embodiment may be included in an apparatus that may be carried by a user, for example, a wearable apparatus. The optical signal processing apparatus 100 may be included in any one of a wristwatch-type apparatus, a bracelet-type apparatus, or a band-type apparatus having a communication function and a data processing function, or may be included in a combination of two or more types.

FIG. 1 is a block diagram showing a configuration of the optical signal processing apparatus 100 (e.g., a spectrometer) according to an exemplary embodiment. It will be understood by one of ordinary skill in the art that general-purpose components other than components shown in FIG. 1 may be further included, and some of the components shown in FIG. 1 may be omitted.

Referring to FIG. 1, the optical signal processing apparatus 100 may include a light source 110, a first sensor array 120, and a second sensor array 130. The optical signal processing apparatus 100 may further include a processor 140. However, according to another exemplary embodiment, the processor 140 may be provided separately from the optical signal processing apparatus 100 including the light source 110, the first sensor array 120, and the second sensor array 130.

The optical signal processing apparatus 100 according to an exemplary embodiment may be used for measuring biometric information. An optical signal incident on a target may include biometric information by reacting with a substance in the target while traveling through the target. Since the optical signal is reflected, absorbed, and scattered according to the intrinsic characteristics of the substance in the target, the optical signal traveling in the target may include intrinsic biometric information. Since the substance in the target may be different depending on a position, optical signals having different trajectories may include different biometric information.

The light source 110 according to an exemplary embodiment may output an optical signal. The optical signal output from the light source 110 may be applied to the target.

The light source 110 may output or emit the optical signal and may be controlled by the processor 140 that controls a traveling direction of the optical signal according to the electrical signal to make the light incident on the target be at a specific incident angle.

The optical signal output from the light source 110 according to an exemplary embodiment may be an optical signal by a laser or a light-emitting diode (LED), but is not limited thereto.

The laser output from the light source 110 may be implemented by, for example, a semiconductor laser diode. In some cases, the light source 110 may employ a short-wavelength light-emitting diode.

The optical signal output from the light source 110 may be different depending on a type of a substance of interest in the target. For example, if the target is a person and the substance of interest is a substance in the skin of the target, the light source 110 may emit red light or light having a wavelength in a near infrared region. A range of the wavelength described above is merely an example, and the light source 110 may emit an optical signal having a different wavelength according to the substance of interest or the like.

In this regard, the target may be a person or an animal but is not limited thereto. The target may be a part included in the target. The substance of interest may be included in the target and may be a substance having an intrinsic optical characteristic. The substance of interest may be a biomaterial or a substance in which the biomaterial is combined with a phosphor or the like. For example, the substance of interest may be a red blood cell, glucose, high sensitivity C-reactive protein (hsCRP), etc., and is not limited thereto.

The substance of interest may differ in absorption, transmission, and reflection of the optical signal depending on a molecular bonding structure, a molecular shape, a potential energy surface (PES), masses of atoms, vibration coupling, etc. Thus, information about the substance of interest, that is, biometric information, may be obtained by identifying a characteristic of light reflected from or transmitted through the substance of interest. An optical signal having an optical characteristic changed by reacting with the substance of interest may be referred to as an optical signal including the biometric information.

The optical signal processing apparatus 100 may include a plurality of image sensors. An image sensor may sense the optical signal. For example, the image sensor may sense detection light obtained by reflecting the optical signal output from the light source 110 to the target. Some of the plurality of image sensors included in the optical signal processing apparatus 100 may constitute one unit. For example, a first number of image sensors included in a first area among the plurality of image sensors included in the optical signal processing apparatus 100 may constitute the first sensor array 120, and a second number of image sensors included in a second area may constitute the second sensor array 130. In this regard, the first number and the second number may be the same or different.

The first sensor array 120 according to an exemplary embodiment may include a plurality of image sensors that obtain a first image signal from detection light obtained from the target according to the optical signal output from the light source 110. Also, the second sensor array 130 according to an exemplary embodiment may include a plurality of image sensors that obtain a second image signal having repeatability with the first image signal from detection light obtained in an area adjacent to the first sensor array 120.

The first image signal may be an image signal obtained by the first sensor array 120. The first image signal may be obtained according to an image signal obtained from the plurality of image sensors included in the first sensor array 120.

Also, the second image signal may be an image signal obtained by the second sensor array 130. The second image signal may be obtained according to an image signal obtained from the plurality of image sensors included in the second sensor array 130.

The sensor arrays 120 and 130 may be image sensors, photodiode arrays, phototransistor arrays, etc.

The sensor arrays 120 and 130 may include image sensors arranged two-dimensionally on an incident surface. Each of the image sensors may include a band-pass-filter that passes only light of a predetermined wavelength band and blocks light outside the predetermined wavelength band. At least some of the image sensors may have pass bands of different wavelengths.

The first sensor array 120 and the second sensor array 130 may be located in adjacent areas. The adjacent areas may share a boundary line, or may have one or more objects between the adjacent areas within a predetermined range. For example, when one area is divided into sixteen areas, two of the sixteen divided areas may be areas adjacent to each other.

The first image signal and the second image signal may have repeatability. Repeatability may include repeatability at a level where a predetermined similarity is recognized as a whole even if some differences exist, as well as a repeat of an exact same pattern or characteristic.

The number of the plurality of image sensors included in the first sensor array 120 and the number of the plurality of image sensors included in the second sensor array 130 may be a predetermined number of units.

For example, the number of units may be 16. When there are 64 image sensors numbered 1 through 64, the $1^{st}$ through $16^{th}$ image sensors may be included in the first sensor array 120, and the $17^{th}$ through $32^{nd}$ image sensors may be included in the second sensor array 130.

As another example, the number of units may be 64. When there are 1024 image sensors numbered 1 through 1024, the $65^{th}$ through $128^{th}$ image sensors may be included in the first sensor array 120, and the $449^{th}$ through $512^{th}$ image sensors may be included in the second sensor 130.

The first sensor array 120 or the second sensor array 130 may detect an optical signal. The first sensor array 120 or the second sensor array 130 may include a depletion layer photo diode, an avalanche photo diode, a photomultiplier tube, and the like. Alternatively, the first sensor array 120 or the second sensor array 130 may be implemented as a CMOS image sensor or a charge-coupled device (CCD) image sensor. The first sensor array 120 or the second sensor array 130 may include a plurality of unit detection units, and may further include an optical filter corresponding to a predetermined wavelength in each of the plurality of unit detection units.

The optical signal processing apparatus 100 may further include barrier ribs disposed between the light source 110 and the first and second sensor arrays 120 and 130. The barrier ribs may be formed of a material capable of blocking an optical signal. The barrier ribs may directly block the optical signal toward the first and second sensor arrays 120 and 130 from the light source 110 without the target.

The light source 110, the first sensor array 120 and the second sensor array 130, and the processor 140 may be mounted in a housing. The housing may be formed of a flexible material adapted to bending of an outer surface of the target. In some cases, the housing may have a shape whereby the housing may be attached to a part in which biometric information of the target may be obtained. For example, when the housing is attached to the wrist or the like, a skin contact surface of the housing may be formed to conform to the shape of the wrist. In this case, the housing may be formed of a hard material.

The skin contact surface of the housing may be provided with an attachment layer having a protruding microstructure. The attachment layer may have a shape simulating a bio-adhesion apparatus such as a gecko. The attachment layer may easily attach the optical signal processing apparatus 100 to the skin of the target (a person), and may be detached after being used. As another example, an adhesive layer formed of an adhesive such as an acrylic adhesive or a silicone adhesive may be provided on the skin contact surface of the housing.

The housing may further include first and second covers that cover the light source 110 and the first and second sensor arrays 120 and 130, respectively. Each of the first and second covers may protect the light source 110 and the sensor arrays 120 and 130 from the outside. Further, the first and second covers may be formed of a material having high light transmittance such that light loss of light passing through the first and second covers is minimized. The first and second covers may be formed of the same material or may be formed of different materials. The first and second covers may overlap with the light source 110 and the first and second sensor arrays 120 and 130 with respect to the traveling direction of the optical signal.

The processor 140 according to an exemplary embodiment may determine the characteristic of the target by using the first image signal and/or the second image signal.

For example, the processor 140 may determine the characteristic of the target by using at least one of the first image signal and the second image signal. For example, the processor 140 may select one of the first and second image signals and determine the characteristic of the target by using the selected image signal. In this case, the processor 140 may select a more appropriate image signal to determine the characteristic of the target among from the first image signal and the second image signal, and may use the selected image signal to determine the characteristic of the target. For example, the processor 140 may determine the characteristic of the target by using an image signal having a higher signal to noise ratio (SNR) among the first image signal and the second image signal.

As another example, the processor 140 may use both the first image signal and the second image signal to determine the characteristic of the target. In one example, the processor 140 may compare the first image signal to the second image signal, and determine the characteristic of the target based on a comparison result.

The processor 140 according to an exemplary embodiment may determine a characteristic of detection light obtained by reflecting or transmitting the optical signal from or through the target by using the first image signal and/or the second image signal and may determine the characteristic of the target according to the determined characteristic of the detection light. For example, the processor 140 may use a matrix transformation algorithm to restore the characteristic of the detection light with respect to the first image signal and/or the second image signal, and determine the characteristic of the target based on the restored characteristic of the detection light.

The processor 140 according to an exemplary embodiment may obtain an analysis result of the first image signal and/or the second image signal and control at least one of the light source 110, the first sensor array 120, and the second sensor array 130 to update an operation method. The at least one of the light source 110, the first sensor array 120, and the second sensor array 130 may update the operation mode under the control of the processor 140. For example, the light source 110 may update at least one of an output angle, intensity, and an output time of optical signal output under the control of the processor 140. As another example, the first sensor array 120 and/or the second sensor array 130 may update an exposure time under the control of the processor 140. In this case, the first sensor array 120 and/or the second sensor array 130 may increase or decrease the exposure time of the detection light.

For example, the processor 140 according to an exemplary embodiment may determine whether to update or change the operation method of the at least one of the light source 110, the first sensor array 120, and the second sensor array 130 according to the SNR. In an example, the processor 140 may update the operation method of the at least one of the light source 110, the first sensor array 120, and the second sensor array 130 when the SNR obtained according to the analysis result of the first image signal and/or the second image signal is less than a threshold value. The processor 140 may maintain the current operation method when the SNR is greater than or equal to the threshold value.

As another example, the processor 140 according to an exemplary embodiment may determine whether to update the operation method of the at least one of the light source 110, the first sensor array 120, and the second sensor array 130 according to a degree of saturation. Saturation may occur when each individual pixel, which functions as a well of electrons, becomes filled up to the maximum charge capacity. The degree of saturation may refer to a color saturation that represents the intensity of color in an image. In an example, the processor 140 may reduce the exposure time of the first sensor array 120 and/or the second sensor array 130 when the degree of saturation obtained according to the analysis result of the first image signal and/or the second image signal is equal to or greater than a threshold value, and increase the exposure time of the first sensor array 120 and/or the second sensor array 130 when the degree of saturation is less than the threshold value.

The optical signal processing apparatus 100 may further include a light separator.

Figure 2:
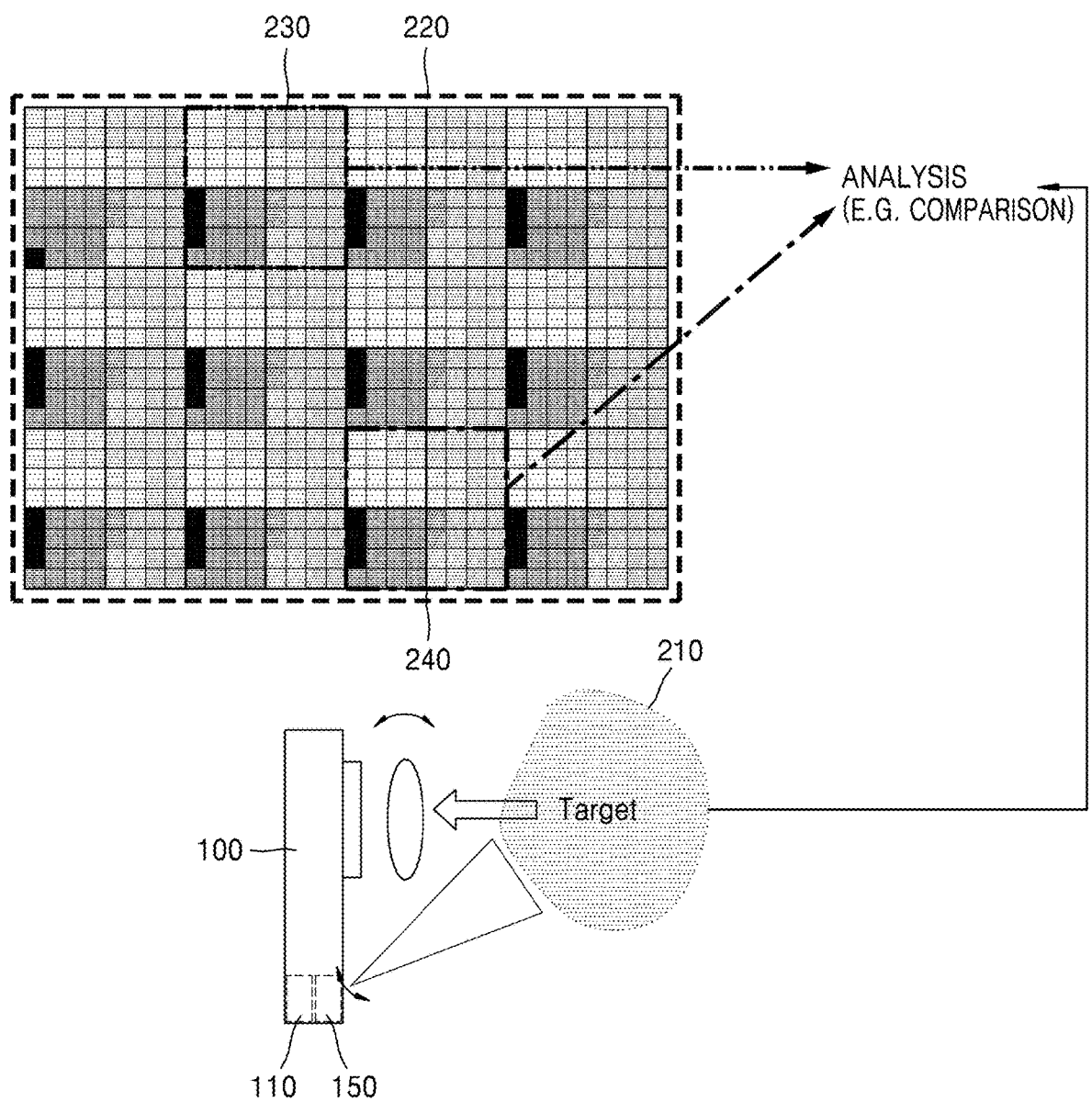
FIG. 2 is a diagram showing an example in which an optical signal processing apparatus according to an exemplary embodiment determines a characteristic of a target by using a plurality of sensor arrays.

FIG. 2 is a diagram showing an example in which the optical signal processing apparatus 100 according to an exemplary embodiment determines a characteristic of a target 210 by using a plurality of sensor arrays. The characteristic of the target 210 may include information of a blood sugar level, a blood cholesterol level, freshness or ageing of foods.

The optical signal processing apparatus 100 according to an exemplary embodiment may output an optical signal to the target 210 by using a light source 110 and obtain detection light that is reflected from or transmitted through the target 210 to obtain wholly or partially an image signal 220.

The image signal 220 may be obtained through a plurality of image sensors. The optical signal processing apparatus 100 may include all or some of the plurality of image sensors used to obtain the image signal 220.

The image signal 220 may include a plurality of image signals. For example, the image signal 220 may include a first image signal 230 and a second image signal 240.

The optical signal processing apparatus 100 according to an exemplary embodiment may determine the characteristic of the target 210 by using all or a part of the image signal 220. For example, the optical signal processing apparatus 100 may determine the characteristic of the target 210 by using at least one of the first image signal 230 and the second image signal 240.

The optical signal processing apparatus 100 according to an exemplary embodiment may further include a light direction controller 150.

The light direction controller 150 may be disposed on a light-emitting surface side of the light source 110. In some cases, an optical device that converts an optical path such as a mirror or a total reflection prism may be disposed between the light source 110 and the light direction controller 150.

The light direction controller 150 may control a direction of light emitted from the light source 110. The light direction controller 150 may control a reflection angle of light reflected by the light direction controller 150 and/or a refraction angle passing through the light direction controller 150 according to an electrical signal. In other words, an optical signal emitted from the light source 110 by the light direction controller 150 may be selectively irradiated to each other in the target 210 at an incident angle.

For example, the light direction controller 150 may include an optical device in which a meta-material, which may change a path of the light to be irradiated, is disposed. The meta-material may be a structure having a plurality of meta-atoms arranged in a fine pattern shape. Depending on a shape and a size of a meta-atom and an arrangement (e.g., a periodic or quasi-periodic arrangement) of the meta-atoms, the meta-material may exhibit various effective properties. The meta-material may be provided on a surface of a piezoelectric body. The piezoelectric body may be provided with first and second electrodes. For example, the piezoelectric body may have a rectangular shape, and the first and second electrodes may be provided on both sides of the piezoelectric body. Since an electric signal, for example, a voltage, is applied to the first and second electrodes by a power source, the piezoelectric body may contract or expand due to a piezoelectric phenomenon. As such, an internal structure (for example, distances of the meta-atoms, the size and the shape of the meta-atom, etc.) of the meta-material may be changed depending on the contraction or expansion of the piezoelectric body.

The light direction controller 150 of the present exemplary embodiment may refract or reflect incident light at a predetermined angle by using the meta-material. For example, when the meta-material has a transmissive structure, the light direction controller 150 may refract the incident light at a predetermined angle. Alternatively, when the meta-material has a reflective structure, the light direction controller 150 may reflect the incident light at a predetermined angle. Further, an angle of refraction or reflection may be changed according to the voltage applied to the first and second electrodes.

The structure of the meta-atom may control a light deflection, and also control a light deflection according to the distances between the meta-atoms. The spacing of the meta-atoms may be adjusted by using an electrical mechanical deformation phenomenon such as a piezoelectric phenomenon of a piezoelectric body.

Figure 3:
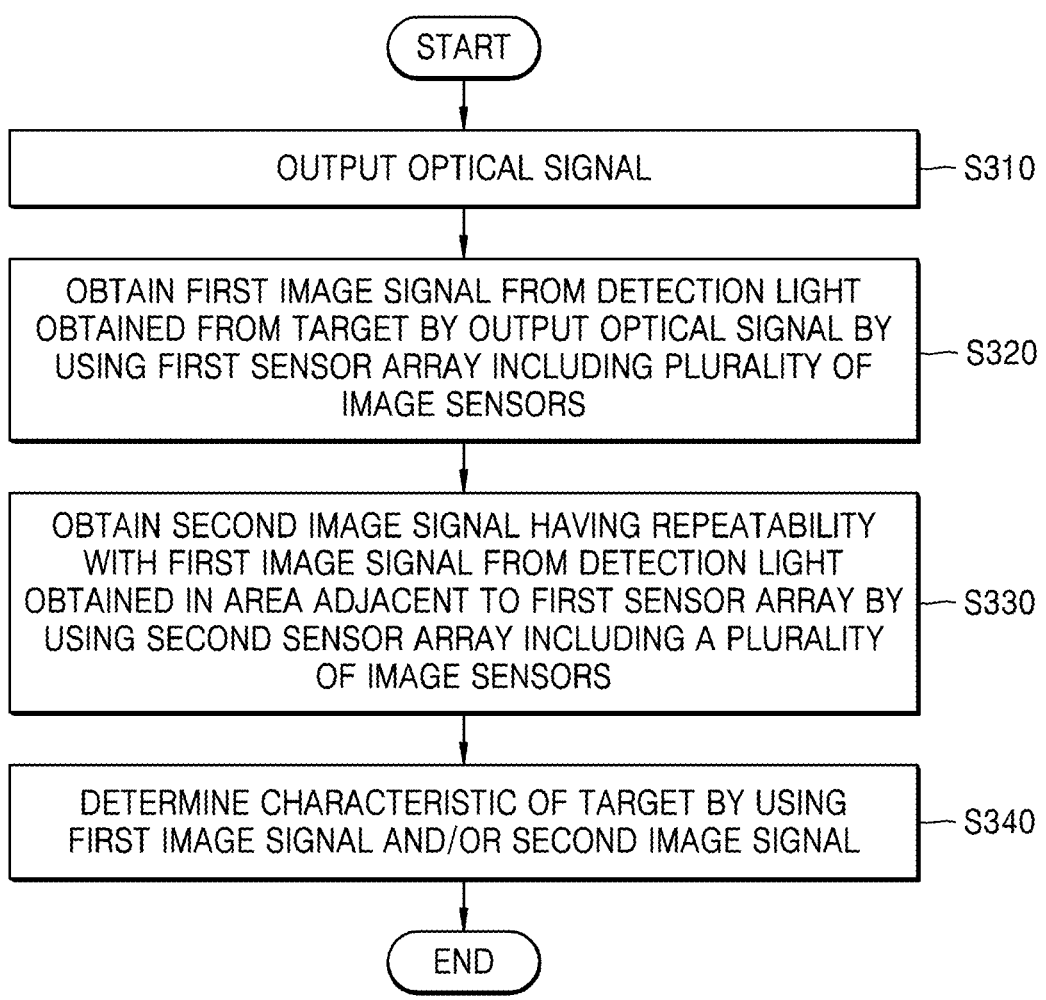
FIG. 3 is a flowchart illustrating a method in which an optical signal processing apparatus determines a characteristic of a target by using a first image signal and a second image signal according to an exemplary embodiment.

FIG. 3 is a flowchart illustrating a method in which the optical signal processing apparatus 100 determines a characteristic of a target by using a first image signal and a second image signal according to an exemplary embodiment.

In operation S310, the optical signal processing apparatus 100 according to an exemplary embodiment outputs an optical signal. The optical signal processing apparatus 100 may output or emit the optical signal toward the target. For example, the optical signal processing apparatus 100 may output a laser or LED light to the target at a specific incident angle, but is not limited thereto.

As a specific method of outputting the optical signal, the description above provided with reference to FIG. 1 may be employed.

In operation S320, the optical signal processing apparatus 100 according to an exemplary embodiment obtains a first image signal from detection light obtained from the target by the output optical signal by using a first sensor array including a plurality of image sensors.

The first sensor array 120 may include a plurality of image sensors. The image sensors may perform a filtering function as well as a sensing function.

The first sensor array 120 may include a first number of image sensors included in a first area of the plurality of image sensors included in the optical signal processing apparatus 100. For example, 64 image sensors are included in the optical signal processing apparatus 100 and 16 image sensors of the first sensor array 120 are included in the first area of the 64 image sensors.

In operation S330, the optical signal processing apparatus 100 according to an exemplary embodiment obtains a second image signal having repeatability with the first image signal from detection light obtained in an area adjacent to the first sensor array by using a second sensor array including a plurality of image sensors.

The second sensor 130 array may include a second number of image sensors included in a second area of the plurality of image sensors included in the optical signal processing apparatus 100. For example, 64 image sensors are included in the optical signal processing apparatus 100 and 16 image sensors are included in the second area of the 64 image sensors included.

The first image signal obtained from the first sensor array 120 and the second image signal obtained from the second sensor array 130 may have repeatability. Even if the first image signal and the second image signal are not completely identical, the first image signal and the second image signal have repeatability at a level at which some similarities are recognized as a whole.

With regard to specific operations of the first sensor array and the second sensor array, the description above provided in FIG. 1 may apply.

In operation S340, the optical signal processing apparatus 100 according to an exemplary embodiment determines the characteristic of the target by using the first image signal and/or the second image signal.

The optical signal processing apparatus 100 may determine the characteristic of the target by using only the first image signal or the second image signal, and may determine the characteristic of the target by using both the first image signal and the second image signal.

With regard to a specific method of determining the characteristic of the target, the description above provided in FIG. 1 may apply.

Figure 4:
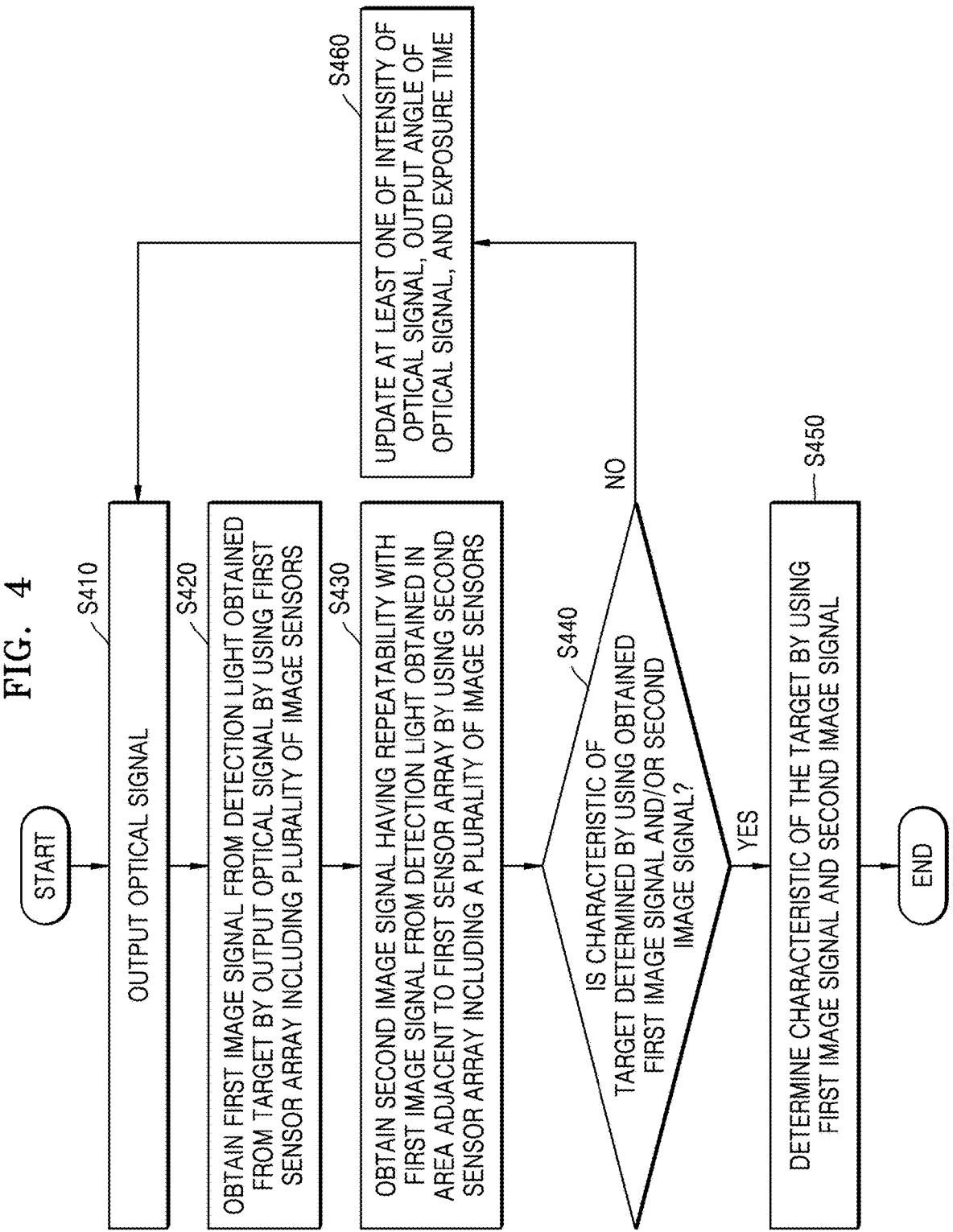
FIG. 4 is a flowchart illustrating a method in which an optical signal processing apparatus determines a characteristic of a target by updating at least one of an intensity of an optical signal, an angle of the optical signal, and an exposure time according to an exemplary embodiment.

FIG. 4 is a flowchart illustrating a method in which the optical signal processing apparatus 100 determines a characteristic of a target by updating at least one of an intensity of an optical signal, an angle of the optical signal, and an exposure time according to an exemplary embodiment.

Referring to FIG. 4, an optical signal processing method according to an exemplary embodiment includes some of the operations shown in FIG. 3. Even if omitted below, the description above with respect to the operations shown in FIG. 3 may also be applied to the optical signal processing method of FIG. 4.

Operations S410 to S430 correspond to operations S310 to S330, and thus detailed descriptions thereof will be omitted for the convenience of simplicity.

In operation S440, the optical signal processing apparatus 100 according to an exemplary embodiment determines whether to determine the characteristic of the target by using a first image signal and/or a second image signal.

The optical signal processing apparatus 100 according to an exemplary embodiment may compare an SNR or a degree of saturation of the first image signal and/or the second image signal with a preset threshold value to determine whether to determine the characteristic of the target by using the first image signal and/or the second image signal according to a comparison result.

For example, when the SNR obtained according to an analysis result of the first image signal and/or the second image signal is less than a threshold value, the optical signal processing apparatus 100 may not determine the characteristic of the target by using the currently obtained first image signal and/or second image signal. In this case, as described in operation S460, the optical signal processing apparatus 100 may update at least one of an intensity of the optical signal, an output angle of the optical signal, and an exposure time to obtain the first image and the second image again. However, when the SNR obtained according to the analysis result of the first image signal and/or the second image signal is equal to or greater than the threshold value, the optical signal processing apparatus 100 may determine the characteristic of the target by using the currently obtained first image signal and/or second image signal as described in operation S450.

As another example, the optical signal processing apparatus 100 may not determine the characteristic of the target by using the currently obtained first image signal and/or second image signal when the degree of saturation obtained according to the analysis result of the first image signal and/or the second image signal is less than a threshold value or is equal to or greater than the threshold value. In this case, as described in operation S460, the optical signal processing apparatus 100 may update at least one of the intensity of the optical signal, the output angle of the optical signal, and the exposure time to obtain the first image and the second image again. However, when the degree of saturation obtained according to the analysis result of the first image signal and/or the second image signal is within a predetermined range, the optical signal processing apparatus 100 may determine the characteristic of the target by using the currently obtained first image signal and/or second image signal as described in operation S450.

In operation S450, the optical signal processing apparatus 100 according to an exemplary embodiment determines the characteristic of the target by using the first image signal and the second image signal.

For example, the optical signal processing apparatus 100 may restore a characteristic of detection light (or reflection light) by using a matrix transformation algorithm with respect to the first image signal and/or the second image signal and determine the characteristic of the target based on the restored characteristic of the detection light (or the reflection light).

In operation S460, the optical signal processing apparatus 100 according to an exemplary embodiment updates at least one of the intensity of the optical signal, the output angle of the optical signal, and the exposure time.

The optical signal processing apparatus 100 according to an exemplary embodiment may update or change the at least one of the intensity of the optical signal, the output angle of the optical signal, and the exposure time according to the analysis result of the first image signal obtained in operation S420 and/or the second image signal obtained in operation S430.

For example, when the SNR obtained according to the analysis result is less than the threshold value, the optical signal processing apparatus 100 may update the output angle of the optical signal. The optical signal processing apparatus 100 may increase or decrease the output angle of the optical signal according to the SNR obtained according to the analysis result.

As another example, the optical signal processing apparatus 100 may reduce the exposure time of the first sensor array 120 and/or the second sensor array 130 when the degree of saturation obtained according to the analysis result is equal to or greater than a threshold value, and increase the exposure time of the first sensor array 120 and/or the second sensor array 130 when the degree of saturation is less than the threshold value.

As another example, when the degree of saturation obtained according to the analysis result is equal to or greater than the threshold value, the optical signal processing apparatus 100 may decrease the intensity of the optical signal and increase the intensity of the optical signal when the degree of saturation is less than the threshold value.

Figure 5:
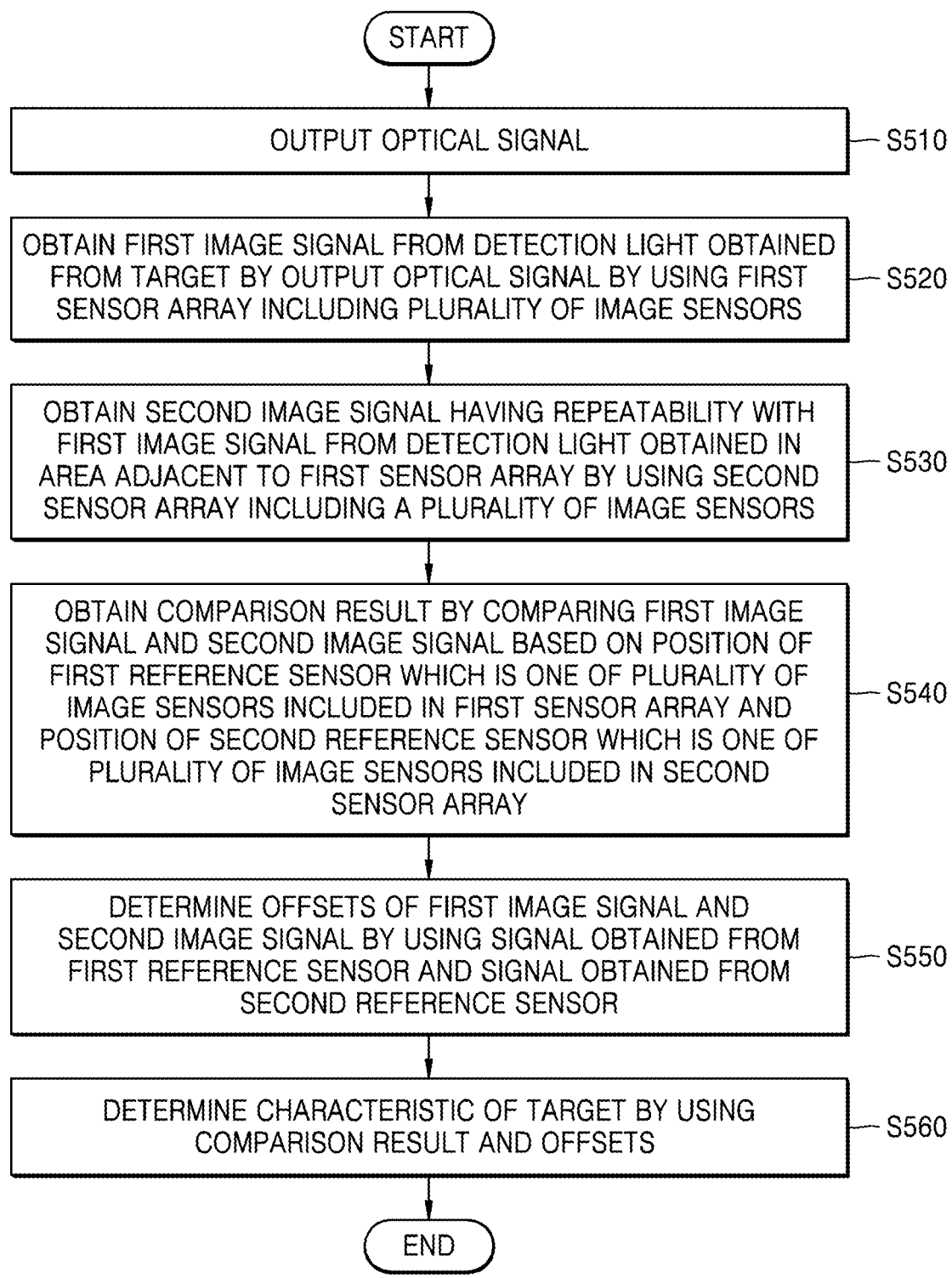
FIG. 5 is a flowchart illustrating a method in which an optical signal processing apparatus determines a characteristic of a target by using a plurality of reference sensors according to an exemplary embodiment.

FIG. 5 is a flowchart illustrating a method in which the optical signal processing apparatus 100 determines a characteristic of a target by using a plurality of reference sensors according to an exemplary embodiment.

Referring to FIG. 5, an optical signal processing method according to an exemplary embodiment includes some of the operations shown in FIG. 3. Even if omitted below, the description above with respect to the operations shown in FIG. 3 may also be applied to the optical signal processing method of FIG. 5.

Operations S510 to S530 correspond to operations S310 to S330, and thus detailed descriptions thereof will be omitted for the convenience of simplicity.

In operation S540, the optical signal processing apparatus 100 according to an exemplary embodiment obtains a comparison result by comparing a first image signal to a second image signal based on a position of a first reference sensor, which is one of a plurality of image sensors included in a first sensor array, and a position of a second reference sensor, which is one of a plurality of image sensors included in a second sensor array.

The plurality of image sensors included in the sensor array may include one or more reference sensors. For example, a lower left image sensor among the plurality of image sensors included in the first sensor array may be the first reference sensor. As another example, a lower left image sensor among the plurality of image sensors included in the second sensor array may be a second reference sensor.

A reference sensor according to an exemplary embodiment may refer to an image sensor in which an optical signal received by covering a metal over the image sensor is wholly or partially blocked. Unlike other image sensors, the reference sensor may be able to compare absolute values by excluding noise generated in the image sensor.

Also, when the reference sensor according to an exemplary embodiment is disposed at a predetermined position, the reference sensor may be used for positional comparison between a plurality of sensor arrays. For example, an area of the plurality of sensor arrays determined by the plurality of image sensors included in the optical signal processing apparatus 100 may be determined with respect to a position of the reference sensor. The reference sensor may be disposed at a predetermined position. For example, the reference sensor may be located at the upper left, the lower left, the upper right, the lower right, the center, etc. of a sensor array.

When the reference sensor is the first reference sensor in the first sensor array and the reference sensor in the second sensor array is the second reference sensor, the optical signal processing apparatus 100 may obtain the first image signal and the second image signal based on the positions of the first reference sensor and the second reference sensor, respectively, among signals obtained from the plurality of image sensors and compare the obtained first image signal and second image signal to obtain a comparison result.

In operation S550, the optical signal processing apparatus 100 determines offsets of the first image signal and the second image signal by using a signal obtained from the first reference sensor and a signal obtained from the second reference sensor.

An offset according to an exemplary embodiment may mean a deviation in the overall signal value.

When the offset of the first image signal and the offset of the second image signal are different from each other, the overall value of the first image signal and the overall value of the second image signal may be different from each other, and a result value of a direct comparison may be inaccurate. In this case, the optical signal processing apparatus 100 may perform comparison or analysis considering the offset. For example, when the overall value of the first image signal is higher than the overall value of the second image signal by a predetermined value or more, the optical signal processing apparatus 100 may totally lower the value of the first image signal and compare the first image signal with the second image signal.

Thus, when an offset of an image signal is determined, the signal obtained from the reference sensor may be used. For example, the optical signal processing apparatus 100 may determine the offset of the first image signal by using the signal obtained from the first reference sensor, and determine the offset of the second image signal by using the signal obtained from the second reference sensor.

In operation S560, the optical signal processing apparatus 100 according to an exemplary embodiment determines the characteristic of the target by using the comparison result in operation S540 and the offsets in operation S550.

For example, the optical signal processing apparatus 100 may adjust the overall values of the first image signal and the second image signal by using the offsets obtained in operation S550 and compare the adjusted first image signal with the adjusted second image signal to determine the characteristic of the target. As a specific algorithm for determining the characteristic of the target using an image signal, known methods may be used. A method of restoring an optical signal received from the target through a matrix operation may be typically used.

Figure 6:
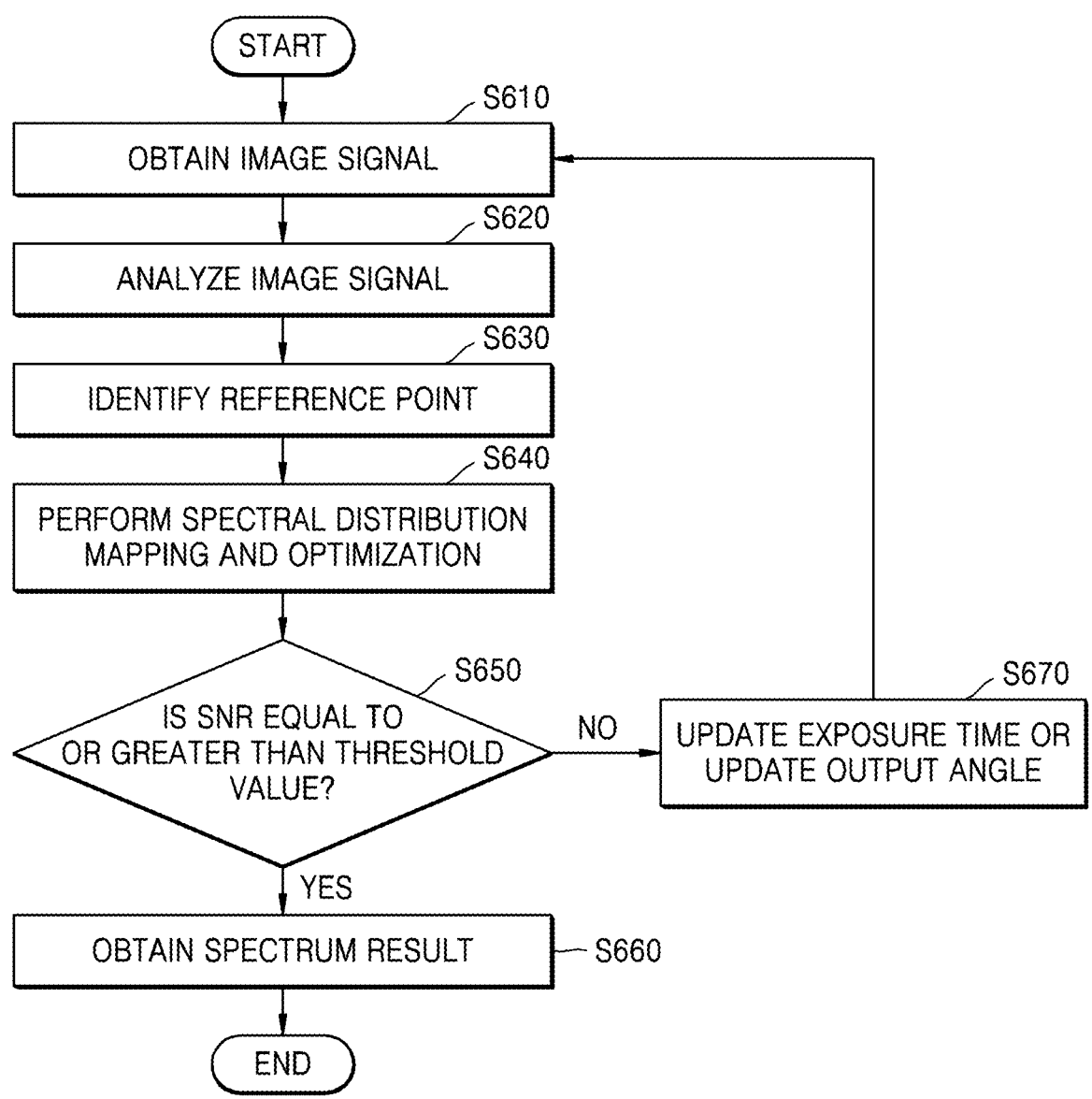
FIG. 6 is a flowchart illustrating a method in which an optical signal processing apparatus determines a characteristic of a target by updating an exposure time or an output angle according to an exemplary embodiment.

FIG. 6 is a flowchart illustrating a method in which the optical signal processing apparatus 100 determines a characteristic of a target by updating an exposure time or an output angle according to an exemplary embodiment.

Referring to FIG. 6, the flowchart of the data obtaining method performed by the optical signal processing apparatus 100 (e.g., a planar spectrometer or a planar spectrometer system) is disclosed. The optical signal processing apparatus 100 may restore a spectrum by analyzing an image signal after obtaining the image signal from an image sensor on which a spectral filter is mounted. After confirming a reference point of a sensor array, a result value of the (full) image sensor is obtained through an appropriate correction. The optical signal processing apparatus 100 may optimize the result value by utilizing plane distribution information of a spectrum from the obtained result value. When an SNR is confirmed in an obtained optimum signal and an appropriate signal is not captured, the optical signal processing apparatus 100 updates an exposure time of the image sensor and a signal obtaining method to carry out a signal obtaining and analysis loop again. In FIG. 6, an algorithm method of enabling optimal spectral data to be obtained by repeating the loop is described.

Specifically, an operation of the optical signal processing apparatus 100 in each operation will be described below.

In operation S610, the optical signal processing apparatus 100 according to an exemplary embodiment obtains an image signal. For example, the optical signal processing apparatus 100 may obtain at least one of a first image signal and a second image signal.

In operation S620, the optical signal processing apparatus 100 according to an exemplary embodiment analyzes the image signal. For example, the optical signal processing apparatus 100 may determine the intensity of light constituting the image signal for each wavelength.

In operation S630, the optical signal processing apparatus 100 according to an exemplary embodiment identifies a reference point. The reference point according to an exemplary embodiment may refer to a position of a reference sensor. One or more reference points may be located for each sensor array.

In operation S640, the optical signal processing apparatus 100 according to an exemplary embodiment may perform spectral distribution mapping and optimization. For example, the optical signal processing apparatus 100 may obtain the intensity of one or more image signals for each wavelength and perform optimization thereon.

In operation S650, the optical signal processing apparatus 100 according to an exemplary embodiment determines whether an SNR is equal to or greater than a threshold value.

In operation S660, the optical signal processing apparatus 100 according to an exemplary embodiment obtains a spectral result based on the image signal when the SNR is equal to or greater than the threshold value.

In operation S670, the optical signal processing apparatus 100 according to an exemplary embodiment updates an exposure time and/or an output angle when the SNR is less than the threshold value.

Figure 7:
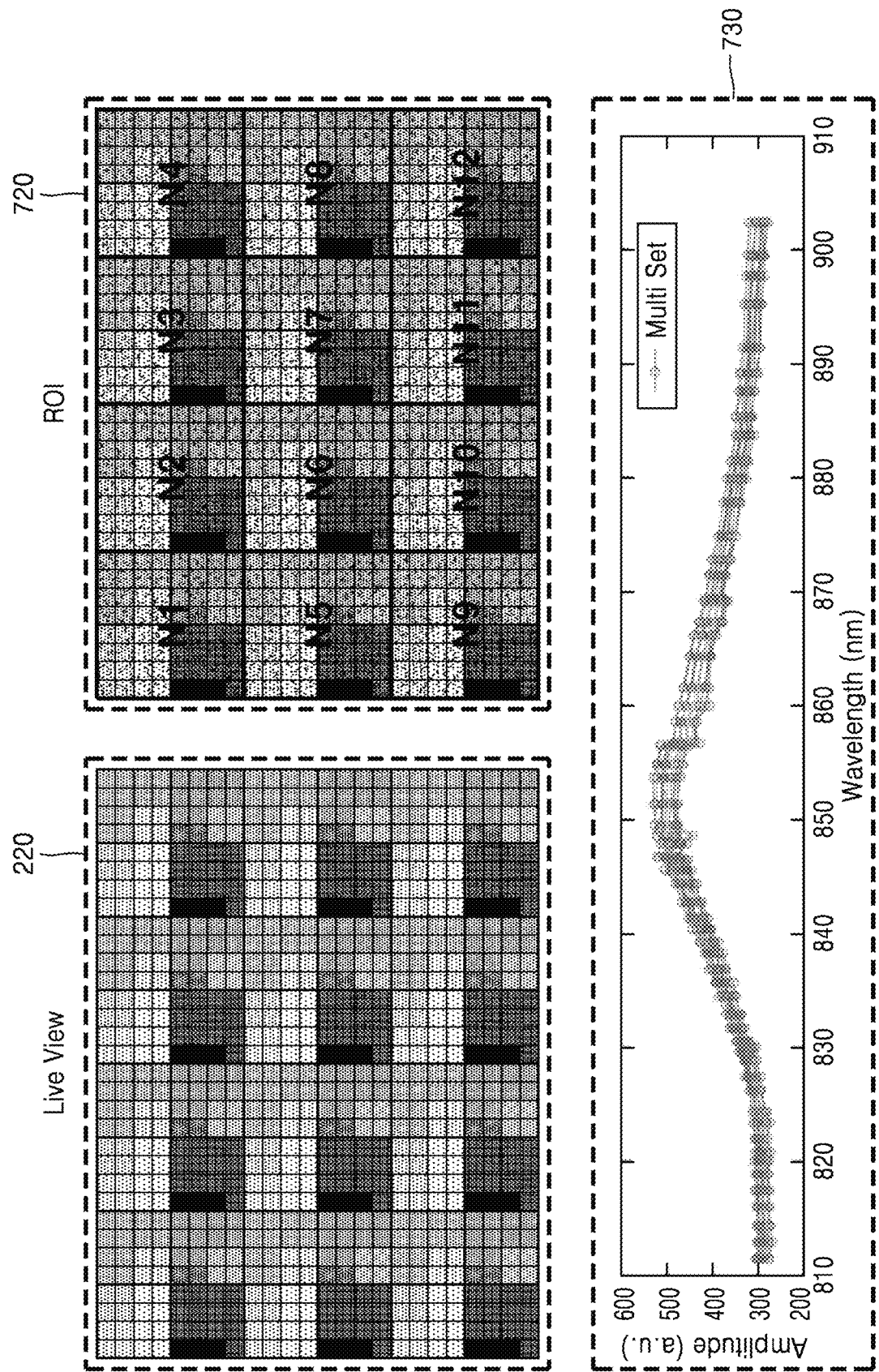
FIG. 7 is a diagram illustrating an example in which an optical signal processing apparatus determines a characteristic of a target by using image signals obtained from a plurality of sensor arrays.

FIG. 7 is a diagram illustrating an example in which the optical signal processing apparatus 100 according to an exemplary embodiment determines a characteristic of a target by using image signals obtained from a plurality of sensor arrays.

The optical signal processing apparatus 100 may constitute one sensor array through a plurality of image sensors in a planar spectroscopic structure but may constitute a plurality of sensor arrays to correct non-uniformity of a spatial distribution of incident light sources. Referring to FIG. 7, the optical signal processing apparatus 100 may divide the plurality of sensor arrays to restore a plurality of image signals.

For example, the optical signal processing apparatus 100 may divide the image signal 220 into twelve to obtain a divided image signal 720. The optical signal processing apparatus 100 may also analyze 12 image signals N1 to N12 included in the divided image signal 720 to obtain 12 graphs 730 representing amplitudes according to wavelengths.

Figure 8:
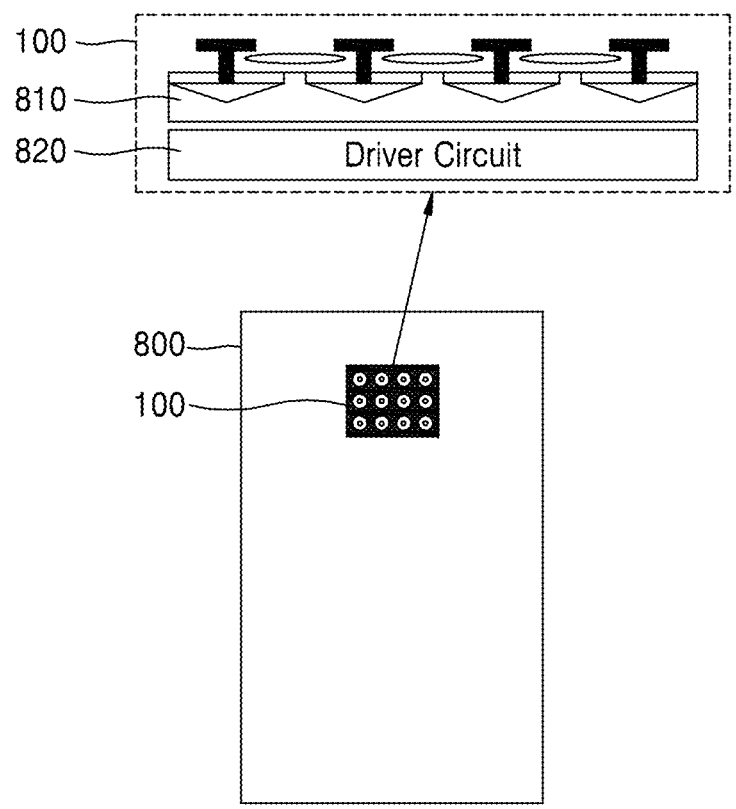
FIG. 8 is a diagram illustrating an example in which an optical signal processing apparatus according to an exemplary embodiment is applied to a mobile device.

FIG. 8 is a diagram illustrating an example in which the optical signal processing apparatus 100 according to an exemplary embodiment is applied to a mobile device 800.

Referring to FIG. 8, the optical signal processing apparatus 100 of the present exemplary embodiment may include an optical device 810 and a driver circuit 820 that drives the optical device 810. The optical device 810 and the driver circuit 820 may be mounted in one housing. The optical signal processing apparatus 100 according to an exemplary embodiment may have a flat plate structure. The driver circuit 820 may be disposed on a rear side of the optical device 810 to have a compact flat plate appearance. Furthermore, the optical signal processing apparatus 100 of the present exemplary embodiment may be integrated as an on-chip.

The optical signal processing apparatus 100 may be connected to an external spectroscopic analyzing apparatus by wire or wirelessly to transmit information detected by the optical signal processing apparatus 100 to the external spectroscopic analyzing apparatus or receive a control instruction from the external spectroscopic analysis apparatus.

The mobile device 800 of the present exemplary embodiment may be a portable device including the optical signal processing apparatus 100. As described above, the optical signal processing apparatus 100 may have a thin flat plate appearance and thus may be mounted on a small electronic device such as a portable device or a mobile device not to protrude or slightly protrude therefrom.

Referring to FIG. 8, the optical signal processing apparatus 100 may be implemented as a planar spectrometer system. The optical signal processing apparatus 100 may obtain an image through a planar sensor structure mounted on the mobile device 800. When the optical signal processing apparatus 100 is implemented as a planar device, the optical signal processing apparatus 100 may have an independent structure including a light source or an external light source dependent structure excluding the light source.

Figure 9:
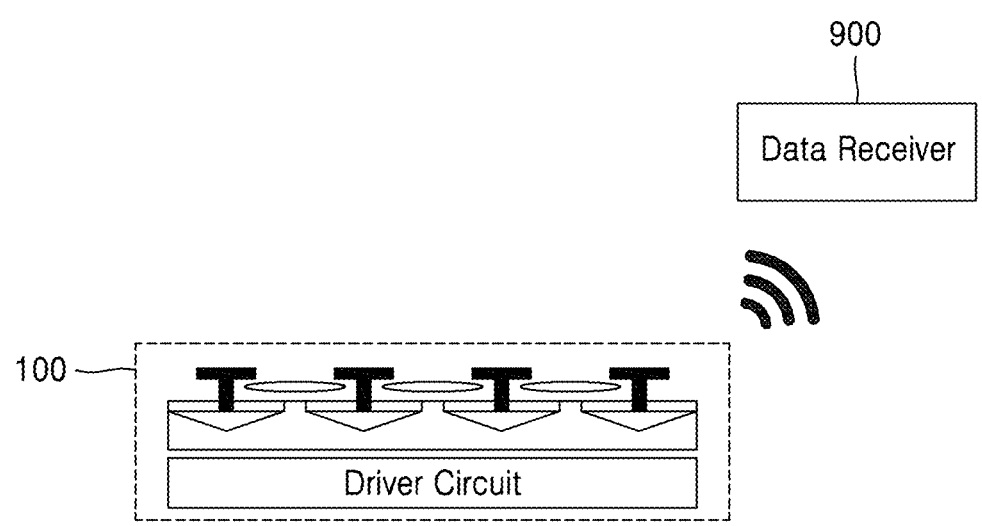
FIG. 9 is a diagram showing an example in which an optical signal processing apparatus according to an exemplary embodiment operates through wireless communication.

FIG. 9 is a diagram showing an example in which the optical signal processing apparatus 100 according to an exemplary embodiment operates through wireless communication.

Referring to FIG. 9, the optical signal processing apparatus 100 according to an exemplary embodiment may operate in conjunction with a data receiver 900. FIG. 9 shows the optical signal processing apparatus 100 of the exemplary embodiment described with reference to FIG. 8, but it is not limited thereto. The optical signal processing apparatus 100 may include a driver circuit 820 and a wireless communication module. The optical signal processing apparatus 100 of the present exemplary embodiment may be integrated as an on-chip to operate as one independent device or transmit data wirelessly to the outside. For example, the optical signal processing apparatus 100 may incorporate Internet of Things (IOT) technology. The data receiver 900 wirelessly collects data detected by the optical signal processing apparatus 100. The data receiver 900 may be a simple data collection device, but is not limited thereto. For example, the data receiver 900 may be a spectroscopic analyzer, a cloud server, a mobile phone, a laptop computer, a personal computer, a server, medical equipment, laboratory equipment, and the like.

Figure 10:
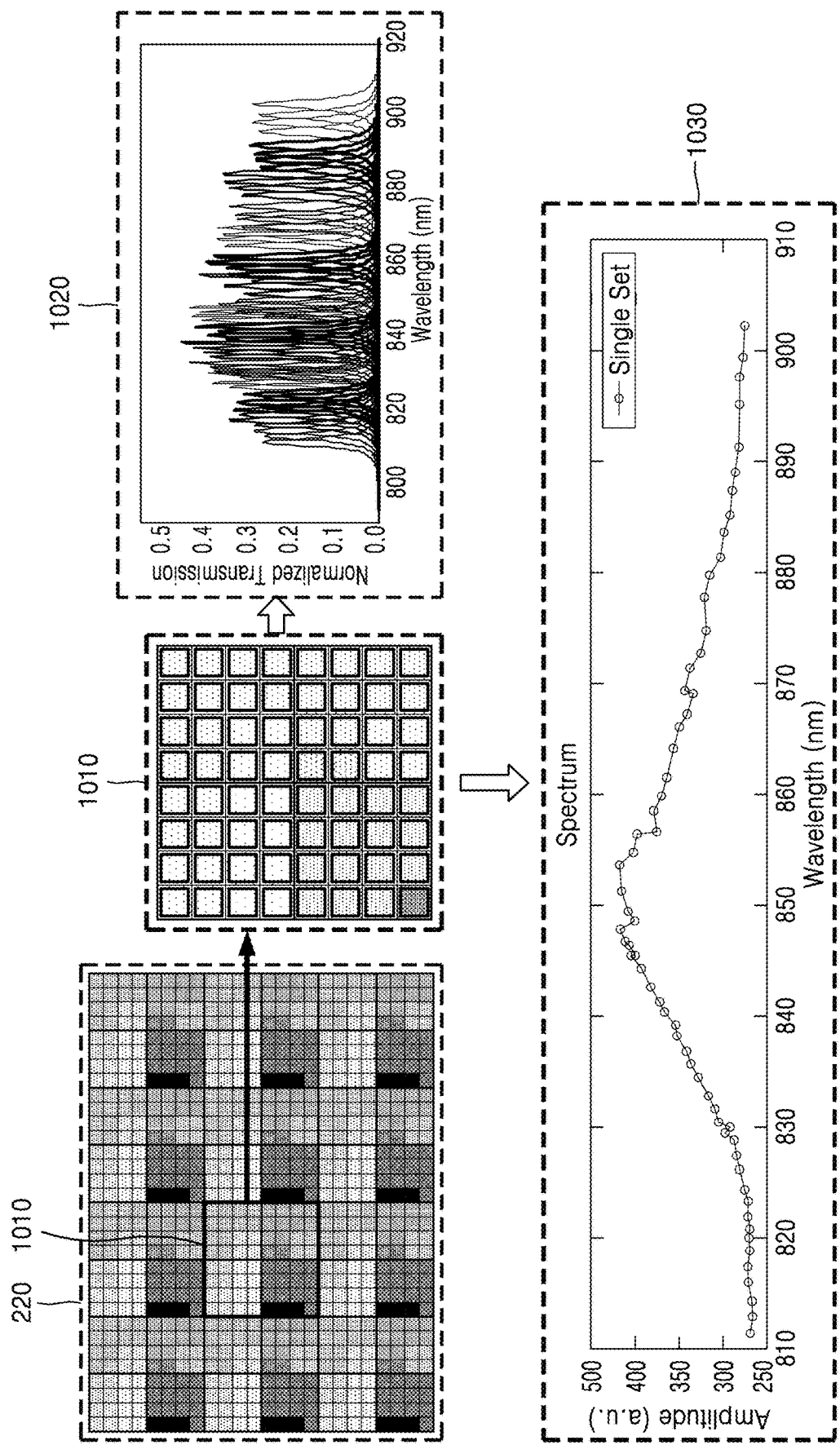
FIG. 10 is a diagram showing an example in which an optical signal processing apparatus according to an exemplary embodiment analyzes an image signal obtained from a sensor array.

FIG. 10 is a diagram showing an example in which the optical signal processing apparatus 100 according to an exemplary embodiment analyzes an image signal obtained from a sensor array.

Referring to FIG. 10, the optical signal processing apparatus 100 may restore a spectrum by analyzing an image obtained from a spectral filter-type image sensor. The optical signal processing apparatus 100 according to an exemplary embodiment may obtain light intensity information from a divided filter box (e.g., the sensor array) and then obtain the image signal 1010 from a filter array and restore a spectrum signal 1030 based on transmission center wavelength in the filter box (e.g., the sensor array). The optical signal processing apparatus 100 may normalize information of the transmission center wavelength and a degree of transmission intensity to ensure uniformity of signals. The optical signal processing apparatus 100 may secure the uniformity of signals by using the normalized degree of transmission intensity. An example of a normalized transmission intensity graph 1020 based on a wavelength is shown in FIG. 10. The filter box is divided into metal lines to prevent interference between filters (e.g., image sensors). The optical signal processing apparatus 100 may restore a signal by utilizing signal information in the filter box.

Figure 11:
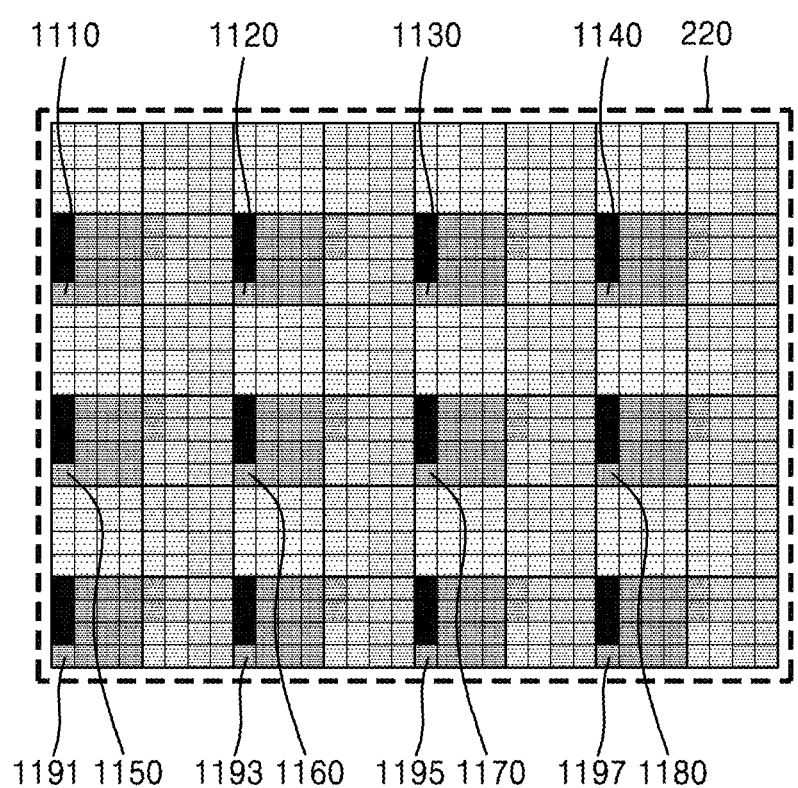
FIG. 11 is a diagram showing an example of an image signal obtained by an optical signal processing apparatus according to an exemplary embodiment.

FIG. 11 is a diagram showing an example of an image signal 220 obtained by the optical signal processing apparatus 100 according to an exemplary embodiment.

The image signal 220 may include one or more reference points 1110, 1120, 1130, 1140, 1150, 1160, 1170, 1180, 1191, 1193, 1195, and 1197. The optical signal processing apparatus 100 may classify and analyze an area of the image signal 220 based on the reference points 1110, 1120, 1130, 1140, 1150, 1160, 1170, 1180, 1191, 1193, 1195, and 1197. The optical signal processing apparatus 100 may correspond image signal information to image sensor information by identifying the reference points 1110, 1120, 1130, 1140, 1150, 1160, 1170, 1180, 1191, 1193, 1195 and 1197 in the image signal 220 through image analysis, identifying information of boundary lines as information of X and Y plane axes, and indexing information of each filter box (e.g., a sensor array).

Figure 12:
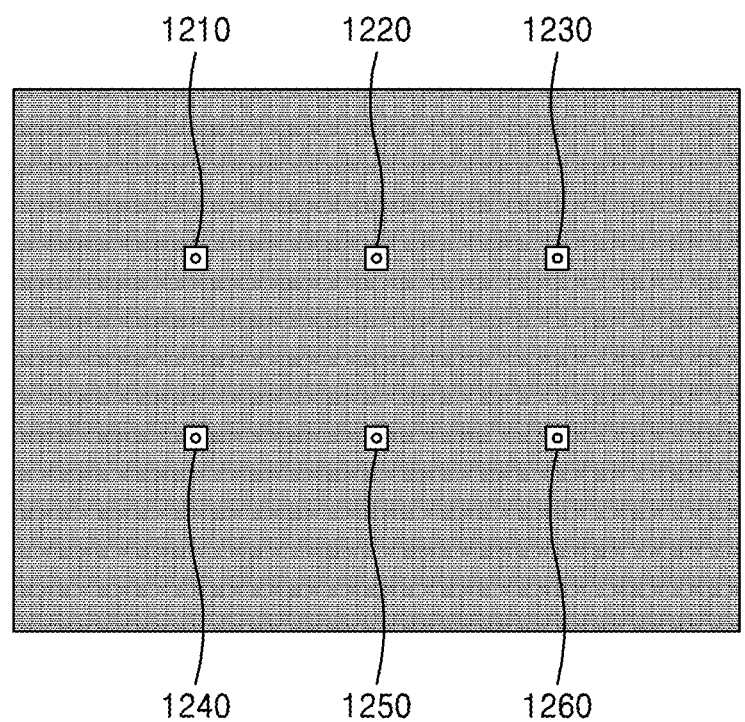
FIG. 12 is a diagram for explaining a plurality of reference points in an image signal obtained by an optical signal processing apparatus according to an exemplary embodiment.

FIG. 12 is a diagram for explaining a plurality of reference points in an image signal obtained by the optical signal processing apparatus 100 according to an exemplary embodiment.

FIG. 12 illustrates reference points 1210, 1220, 1230, 1240, 1250 and 1260 on the other side. Referring to FIG. 12, the reference points 1210, 1220, 1230, 1240, 1250, and 1260 may be expressed in white.

Figure 13:
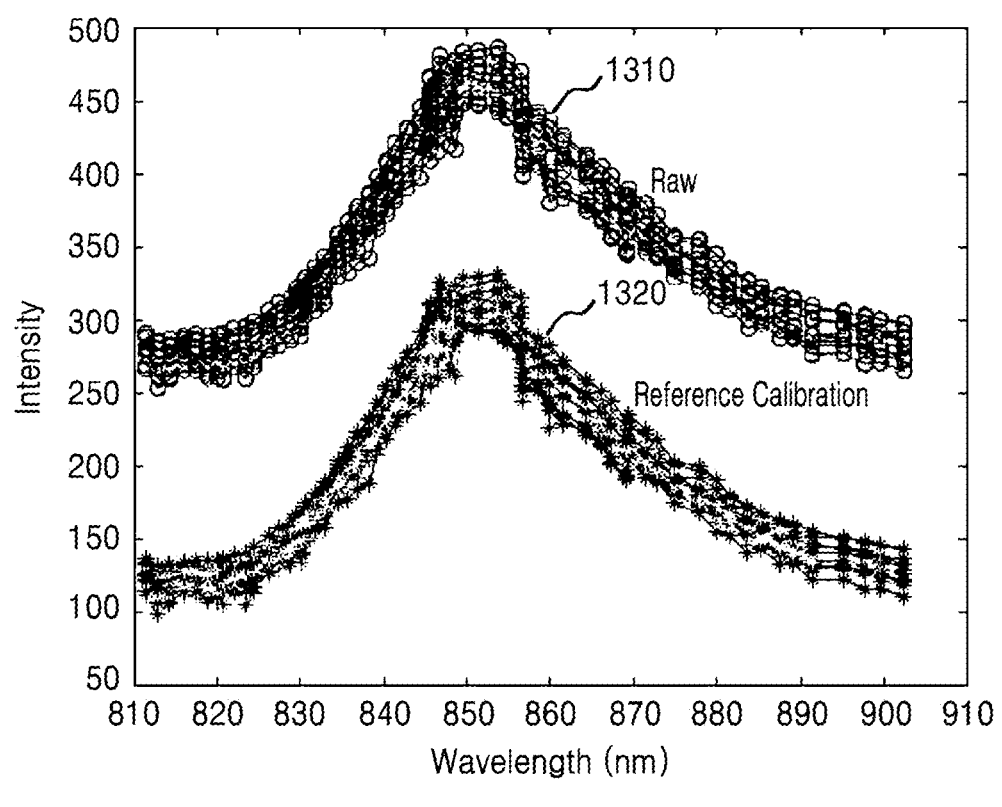
FIG. 13 is a diagram illustrating an example in which an optical signal processing apparatus according to an exemplary embodiment analyzes a signal by using a reference point.

FIG. 13 is a diagram illustrating an example in which the optical signal processing apparatus 100 according to an exemplary embodiment analyzes a signal by using a reference point.

The optical signal processing apparatus 100 may compare amplitude information of a spectral spectrum according to the reference point through a signal obtained from a metal box (e.g., a sensor array) in spectral spectrum information obtained from an image signal.

Since light applied to an image sensor located at the reference point is wholly or partially blocked, a device characteristic such as dark noise of the image sensor may be reflected in a signal obtained by the image sensor located at the reference point. Therefore, the optical signal processing apparatus 100 may perform correction using the signal obtained at the reference point when comparing the amplitude information of the spectral spectrum information.

For example, the optical signal processing apparatus 100 may convert raw-data 1310 into correction data 1320 by correcting the raw-data 1310 according to the signal obtained at the reference point.

Figure 15:
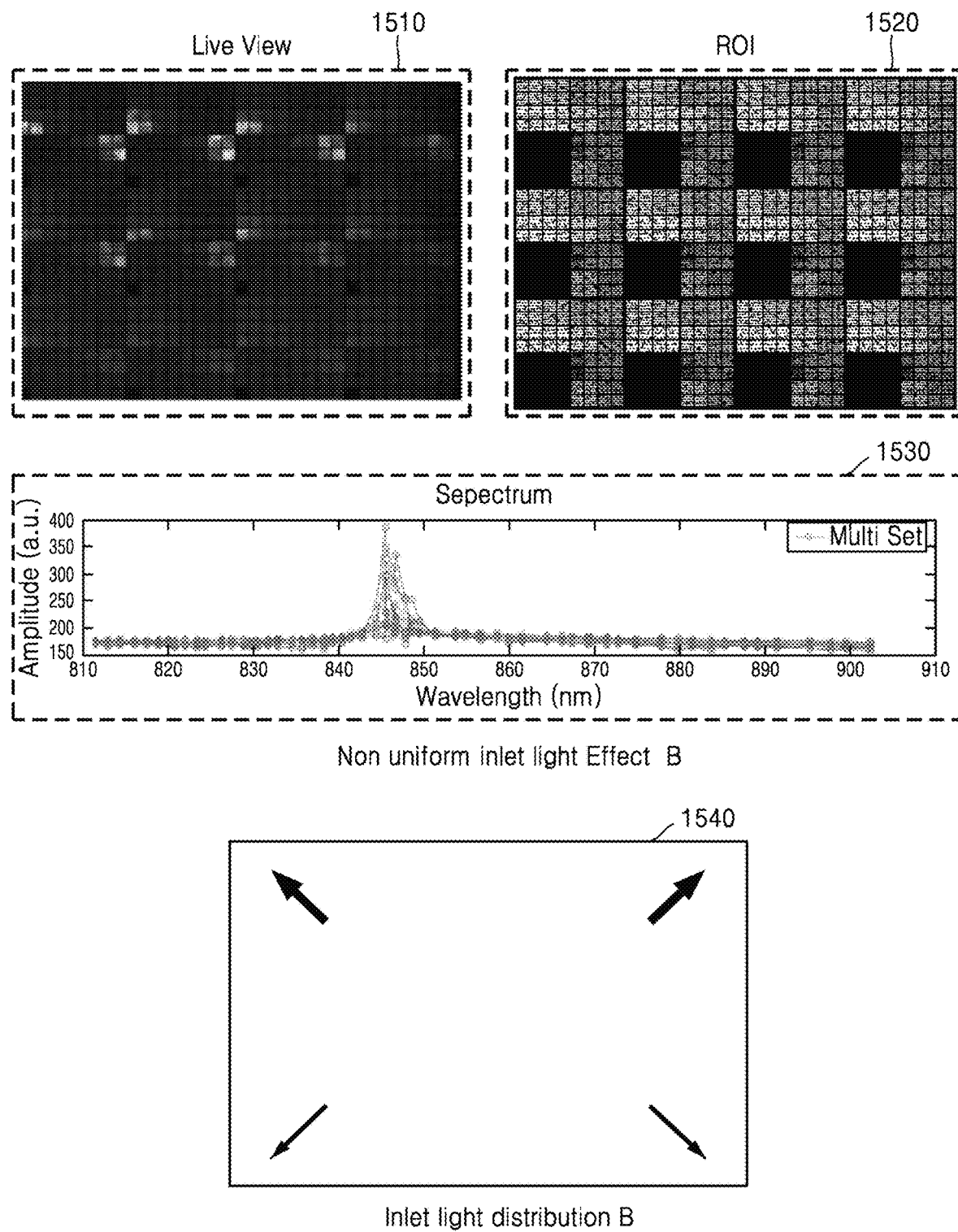
FIG. 15 is a diagram illustrating an example in which an optical signal processing apparatus according to an exemplary embodiment analyzes an image signal when light is not relatively uniformly distributed.

FIG. 14 is a diagram illustrating an example in which the optical signal processing apparatus 100 according to an exemplary embodiment analyzes an image signal when light is relatively uniformly distributed. FIG. 15 is a diagram illustrating an example in which the optical signal processing apparatus 100 according to an exemplary embodiment analyzes an image signal when light is not relatively uniformly distributed.

In a first image signal 1410 and a divided first image signal 1420, a shape of relatively uniform detection light may be identified. Also, in a second image signal 1510 and a divided second image signal 1520, a shape of relatively non-uniform detection light may be identified. Each of a first light distribution diagram 1440 and a second light distribution diagram 1540 schematically illustrates a light distribution state.

In a first graph 1430 according to analysis of the first image signal 1410, a spatial distribution is relatively uniformly spread, but in a second graph 1530 according to analysis of the second image signal 1510, a phenomenon in which a distribution tilts to one side may be identified. Such a characteristic may be a drawback that when a signal average of the second image signal 1510 is simply determined, the amplitude of an originally tilted signal is lowered and thus information is lost. Therefore, the optical signal processing apparatus 100 may utilize such an inhomogeneous light source distribution characteristic to analyze a signal (e.g., an image signal) or to update a signal obtaining method (e.g., update an optical signal output angle).

Figure 16:
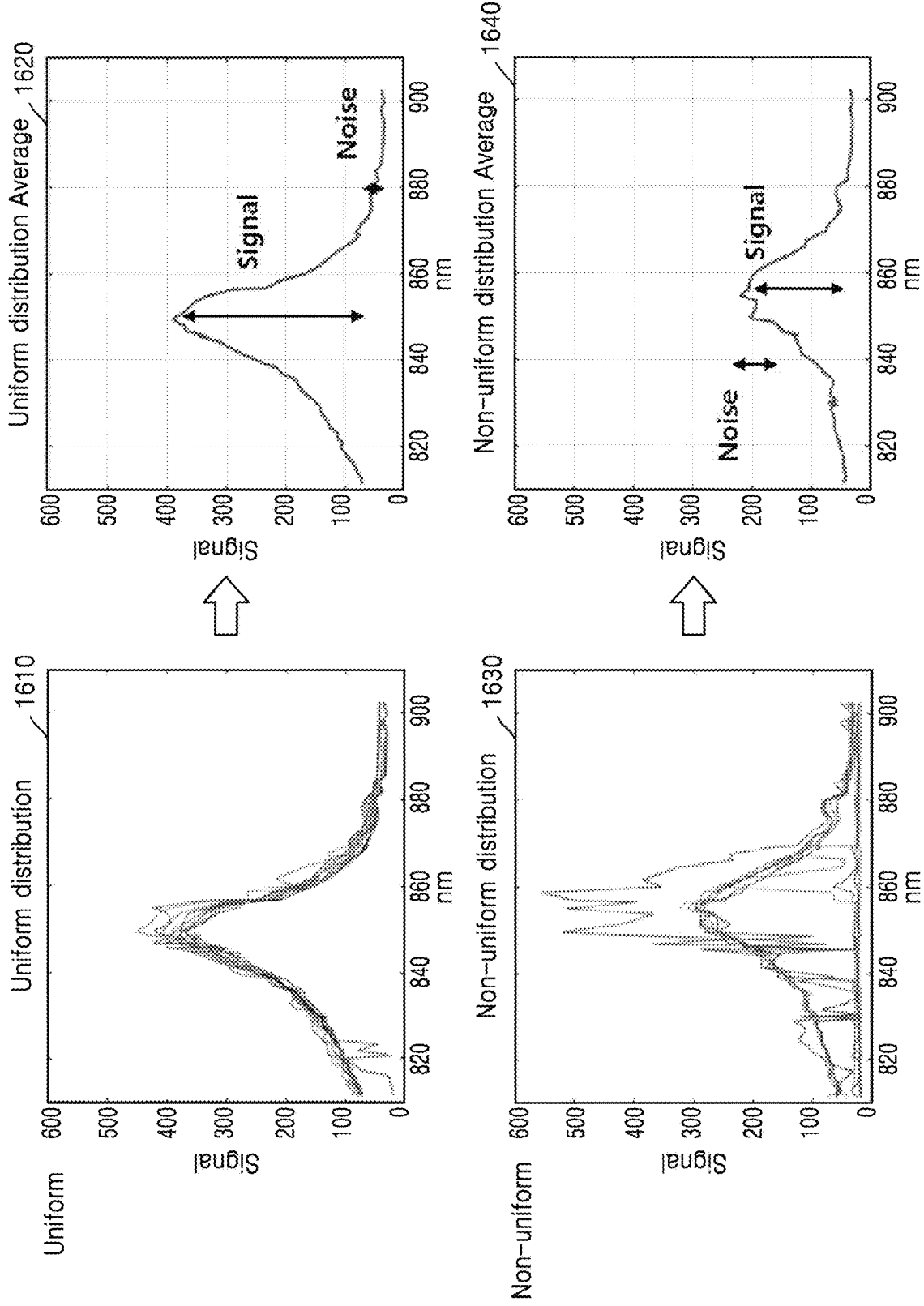
FIG. 16 is a diagram illustrating an example in which an optical signal processing apparatus according to an exemplary embodiment analyzes an image signal when light is relatively uniformly distributed and when light is not relatively uniformly distributed.

FIG. 16 is a diagram illustrating an example in which the optical signal processing apparatus 100 according to an exemplary embodiment analyzes an image signal when light is relatively uniformly distributed and when light is not relatively uniformly distributed.

According to an exemplary embodiment, when detection light obtained in a sensor array is relatively uniform (e.g., when uniformity of the detection light obtained in the sensor array is greater than a predetermined uniformity), a signal size of the detection light obtained by each image sensor for each wavelength may be represented as in a first graph 1610. Also, according to an exemplary embodiment, when the detection light obtained in the sensor array is relatively non-uniform (e.g., when uniformity of the detection light obtained in the sensor array is lower than a predetermined uniformity), the signal size of the detection light obtained by each image sensor for each wavelength may be represented as in a second graph 1630.

When the detection light obtained in the sensor array is relatively uniform, as may be seen from a first SNR graph 1620, an SNR is relatively high, and when the detection light obtained in the sensor array is relatively non-uniform, as may be seen from a second SNR graph 1640, the SNR may be relatively low.

Figure 17:
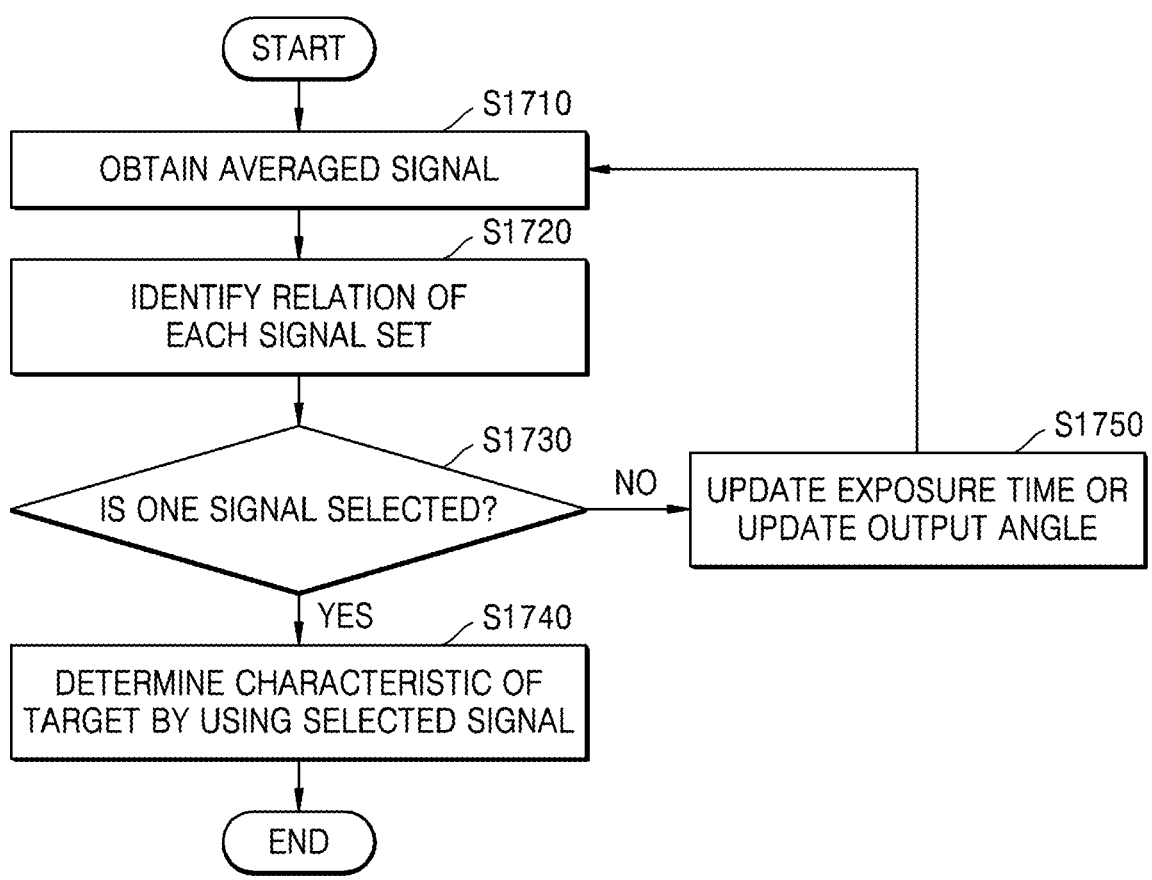
FIG. 17 is a diagram for explaining a method in which an optical signal processing apparatus according to an exemplary embodiment selects one of a plurality of signals (e.g., a plurality of image signals) to determine a characteristic of a target.

FIG. 17 is a diagram for explaining a method in which the optical signal processing apparatus 100 according to an exemplary embodiment selects one of a plurality of signals (e.g., image signals) to determine a characteristic of a target.

In operation S1710, the optical signal processing apparatus 100 according to an exemplary embodiment may obtain an averaged signal from a signal (e.g., an image signal) obtained by a sensor array. For example, the optical signal processing apparatus 100 may obtain an averaged signal of each of a first image signal 1410 obtained from a first sensor array and a second image signal 1510 obtained from a second sensor array.

In operation S1720, the optical signal processing apparatus 100 according to an exemplary embodiment may identify a relation of each signal set. For example, the optical signal processing apparatus 100 may confirm a relation between the first image signal 1410 and the second image signal 1510.

In operation S1730, the optical signal processing apparatus 100 according to an exemplary embodiment may determine whether to select one of the plurality of signals or to re-receive the signal. For example, the optical signal processing apparatus 100 may select one of the first image signal 1410 and the second image signal 1510, analyze the selected image signal, and determine the characteristic of the target by using an analysis result. As another example, the optical signal processing apparatus 100 may analyze a newly obtained image signal by updating an optical signal output angle or the like and determine the characteristic of the target by using an analysis result.

In operation S1740, the optical signal processing apparatus 100 according to an exemplary embodiment may select one of the plurality of signals and determine the characteristic of the target by using the selected signal.

In operation S1750, the optical signal processing apparatus 100 according to an exemplary embodiment may update an exposure time or the optical signal output angle. For example, the optical signal processing apparatus 100 may increase or decrease the exposure time when the sensor array is exposed to detection light. Alternatively, the optical signal processing apparatus 100 may increase or decrease the output angle at which the optical signal is output. The optical signal processing apparatus 100 may determine an increase amount of the exposure time, a decrease amount of the exposure time, an increase amount of the output angle, and a decrease amount of the output angle in accordance with information obtained in operation S1710 or S1720.

Figure 18:
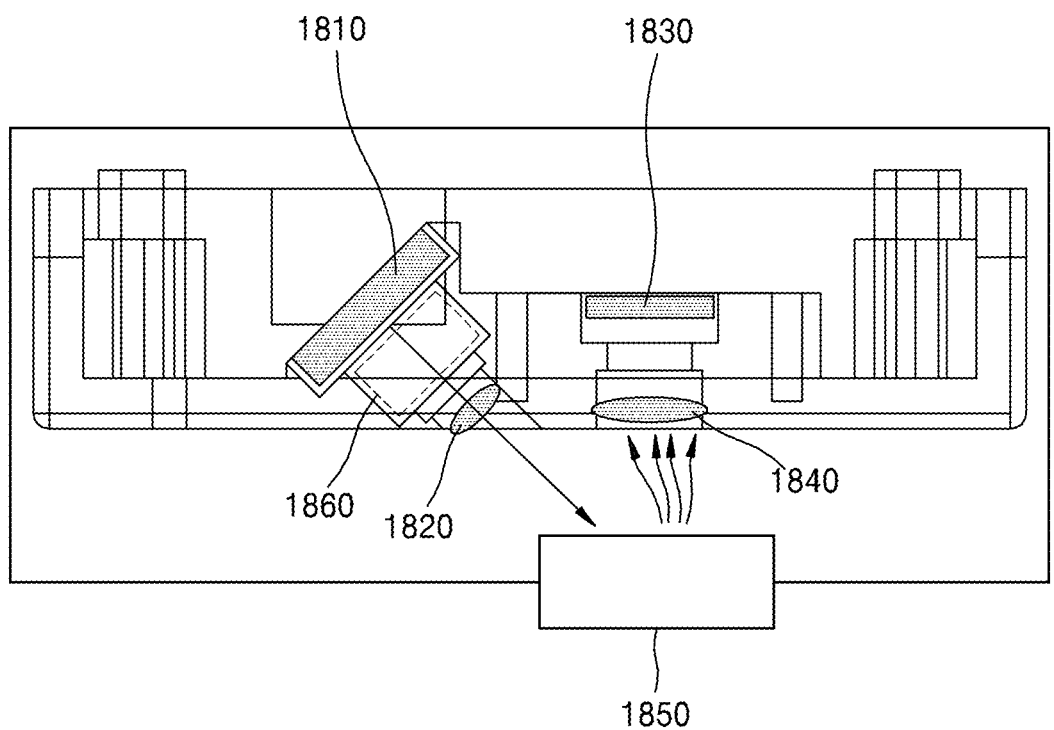
FIG. 18 is a diagram showing an example of a configuration of an optical signal processing apparatus according to an exemplary embodiment.

FIG. 18 is a diagram showing an example of a configuration of the optical signal processing apparatus 100 according to an exemplary embodiment.

A light source 1810 according to an exemplary embodiment may output a light (e.g., a laser) to a target 1850 through a lens 1820. An angle at which the light is incident to the target 1850 may be a predetermined value (e.g., 45 degrees) or may be determined under control of the optical signal processing apparatus 100.

The optical signal processing apparatus 100 may further include a light direction controller 1860 to control a direction of the light emitted from the light source 1810.

The light scattered, reflected, or refracted from the target 1850 may travel to a lens 1840. The optical signal processing apparatus 100 may determine a characteristic of the target 1850 by analyzing the light incident onto the lens 1840 and detected by an image sensor 1830. For example, the optical signal processing apparatus 100 may determine the characteristic of the target 1850 by analyzing the amplitude of the light detected by the image sensor 1830 for each wavelength of the light.

Figure 19:
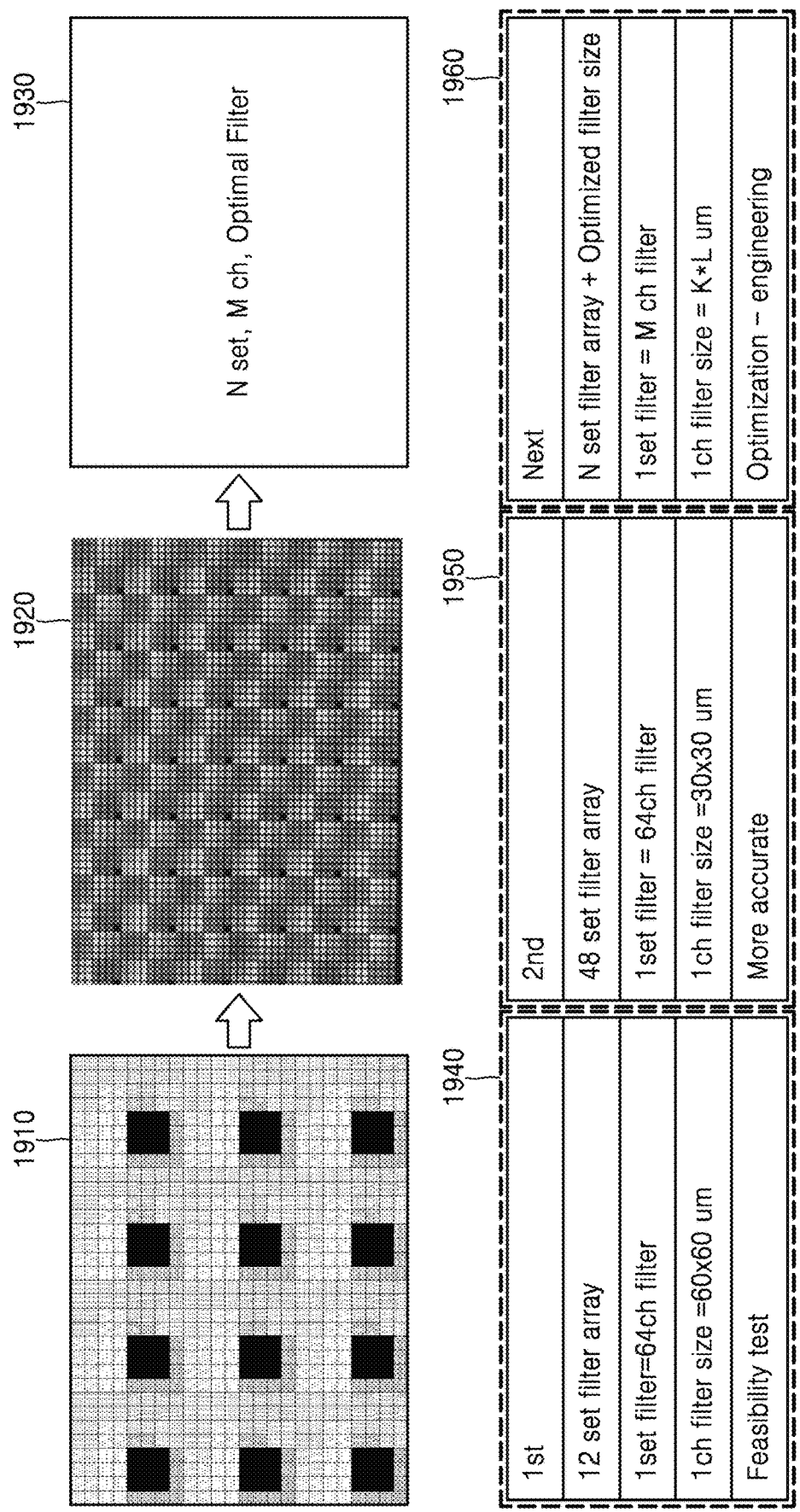
FIG. 19 is a diagram showing an example in which an optical signal processing apparatus according to an exemplary embodiment determines the number of sensor arrays.

FIG. 19 is a diagram showing an example in which the optical signal processing apparatus 100 according to an exemplary embodiment determines the number of sensor arrays.

The number of sensor arrays included in the optical signal processing apparatus 100 may be preset or may be changed according to control. For example, the optical signal processing apparatus 100 may activate a certain number of sensors and deactivate the rest of the sensors in the sensor array, A first image signal 1910 may be obtained when the optical signal processing apparatus 100 includes 12 sensor arrays according to an exemplary embodiment. When the optical signal processing apparatus 100 includes the 12 sensor arrays, the optical signal processing apparatus 100 may have characteristics as shown in a first table 1940.

A second image signal 1920 may be obtained when the optical signal processing apparatus 100 includes 48 sensor arrays according to an exemplary embodiment. When the optical signal processing apparatus 100 includes the 48 sensor arrays, the optical signal processing apparatus 100 may have characteristics as shown in a second table 1950.

A third image signal 1930 may be obtained when the optical signal processing apparatus 100 includes N sensor arrays according to an exemplary embodiment. When the optical signal processing apparatus 100 includes the N sensor arrays, the optical signal processing apparatus 100 may have characteristics as shown in a third table 1960.

The optical signal processing apparatus 100 may determine the number of sensor arrays included in the optical signal processing apparatus 100, the number of image sensors 1830 included in one sensor array, and the like according to an exemplary embodiment. For example, the optical signal processing apparatus 100 may determine the number of the most optimized sensor arrays for determining a characteristic of a target and the number of image sensors 1830 included in one sensor array.

Figure 20:
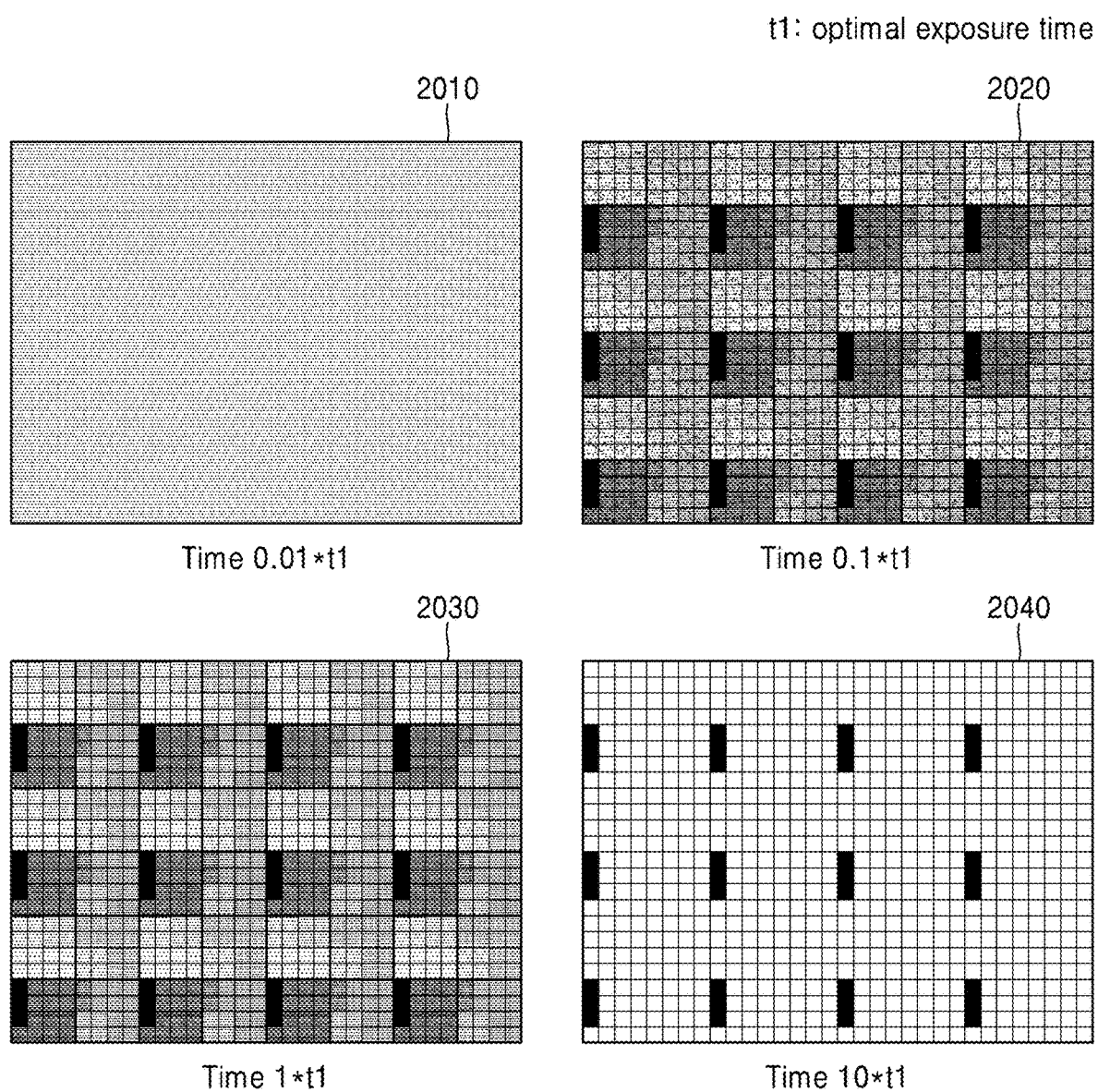
FIG. 20 is a diagram showing an example of image signals obtained by an optical signal processing apparatus according to an exemplary embodiment depending on an exposure time.

FIG. 20 is a diagram showing an example of image signals obtained by the optical signal processing apparatus 100 according to an exemplary embodiment depending on an exposure time.

Referring to FIG. 20, according to an example, a first image signal 2010 obtained when the exposure time is 0.01 times t1, a second image signal 2020 obtained when the exposure time is 0.1 times t1, a third image signal 2030 obtained when the exposure time is 1 time t1, and a fourth image signal 2040 obtained when the exposure time is 10 times t1 are shown.

The optical signal processing apparatus 100 may analyze an obtained image signal to determine an appropriate exposure time. In an example, the optical signal processing apparatus 100 may obtain the first image signal 2010 to the fourth image signal 2040 and may use the third image signal 2030 to determine a characteristic of a target.

Figure 21:
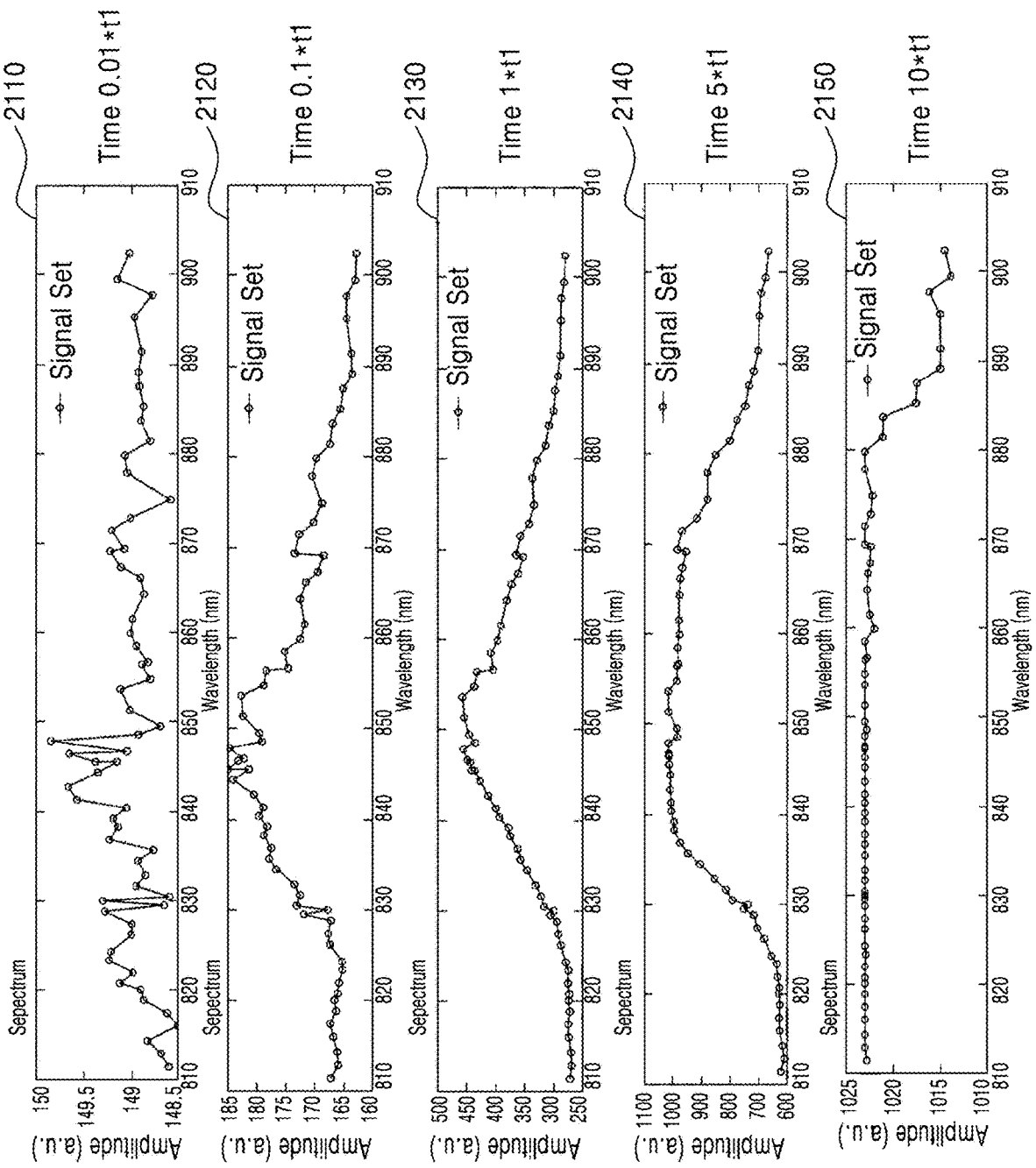
FIG. 21 is a diagram showing an example of an analysis result of image signals obtained by an optical signal processing apparatus according to an exemplary embodiment depending on an exposure time.

FIG. 21 is a diagram showing an example of an analysis result of image signals obtained by the optical signal processing apparatus 100 according to an exemplary embodiment depending on an exposure time.

Referring to FIG. 21, according to an example, a first graph 2110 shows an amplitude per wavelength obtained when the exposure time is 0.01 times t1, a second graph 2120 shows an amplitude per wavelength obtained when the exposure time is 0.1 times t1, a third graph 2130 shows an amplitude per wavelength obtained when the exposure time is 1 time t1, a fourth graph 2140 shows an amplitude per wavelength obtained when the exposure time is 5 times t1, and a fifth graph 2150 shows an amplitude per wavelength obtained when the exposure time is 10 times t1.

The optical signal processing apparatus 100 may analyze the obtained first image signal and update the exposure time according to the analysis result to newly obtain the second image signal. For example, the optical signal processing apparatus 100 may reduce the exposure time when the obtained first image signal is analyzed as shown in the fifth graph 2150. As another example, the optical signal processing apparatus 100 may increase the exposure time when the obtained first image signal is analyzed as shown in the first graph 2110.

Figure 22:
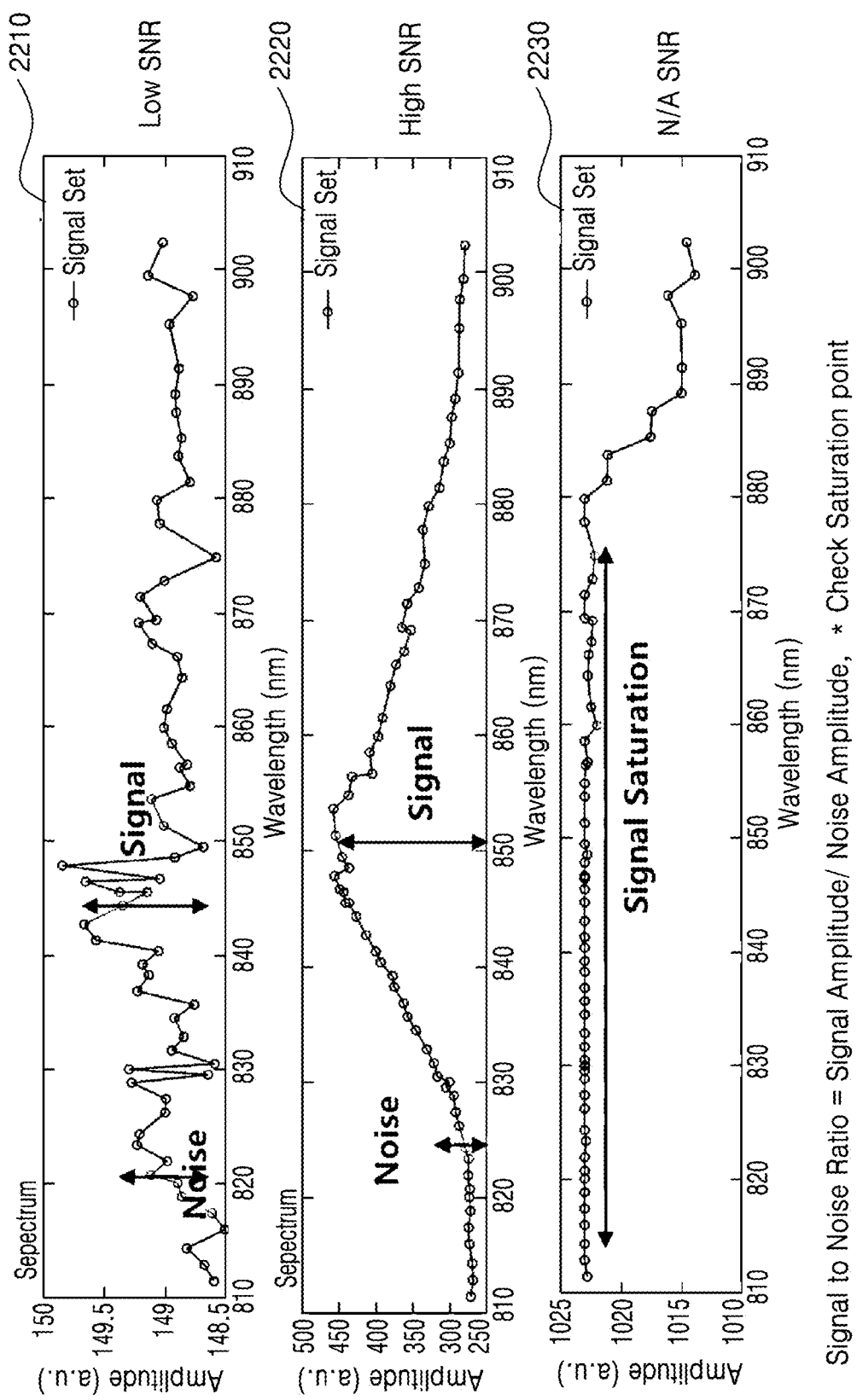
FIG. 22 is a diagram showing an example of an analysis result of image signals obtained by an optical signal processing apparatus according to an exemplary embodiment depending on a signal to noise ratio (SNR).

FIG. 22 is a diagram showing an example of an analysis result of image signals obtained by the optical signal processing apparatus 100 according to an exemplary embodiment depending on an SNR.

Referring to FIG. 22, according to an example, a first graph 2210 which represents an amplitude per wavelength obtained when the SNR is low, a second graph 2220 which represents an amplitude per wavelength obtained when the SNR is high, and a third graph 2230 which represents an amplitude per wavelength obtained when it is substantially difficult to measure SNR are shown.

The optical signal processing apparatus 100 may analyze the obtained first image signal and update an irradiation angle of an optical signal or an exposure time according to an analysis result to newly obtain the second image signal. For example, the optical signal processing apparatus 100 may reduce the irradiation angle of the optical signal when the obtained first image signal is analyzed as shown in the first graph 2210. As another example, the optical signal processing apparatus 100 may reduce the exposure time when the obtained first image signal is analyzed as shown in the third graph 2230.

An optical signal processing apparatus according to an exemplary embodiment may determine a characteristic of a target by using a plurality of sensor arrays.

While not restricted thereto, an exemplary embodiment can be embodied as computer-readable code on a computer-readable recording medium. The computer-readable recording medium is any data storage device that can store data that can be thereafter read by a computer system. Examples of the computer-readable recording medium include read-only memory (ROM), random-access memory (RAM), CD-ROMs, magnetic tapes, floppy disks, and optical data storage devices. The computer-readable recording medium can also be distributed over network-coupled computer systems so that the computer-readable code is stored and executed in a distributed fashion. Also, an exemplary embodiment may be written as a computer program transmitted over a computer-readable transmission medium, such as a carrier wave, and received and implemented in general-use or special-purpose digital computers that execute the programs. Moreover, it is understood that in exemplary embodiments, one or more units of the above-described apparatuses and devices can include circuitry, a processor, a microprocessor, etc., and may execute a computer program stored in a computer-readable medium.

The foregoing exemplary embodiments are merely exemplary and are not to be construed as limiting. The present teaching can be readily applied to other types of apparatuses. Also, the description of the exemplary embodiments is intended to be illustrative, and not to limit the scope of the claims, and many alternatives, modifications, and variations will be apparent to those skilled in the art.

What is claimed is:

1. An apparatus for processing an optical signal, the apparatus comprising:
    a light source configured to output a light;
    a first sensor array disposed on a two dimensional surface and comprising a plurality of first image sensors configured to obtain a first image signal by detecting the light that is scattered, reflected, or refracted from a target;
    a second sensor array disposed to share a boundary with the first sensor array on the same two dimensional surface, the second sensor array comprising a plurality of second image sensors configured to obtain a second image signal having repeatability with the first image signal by detecting the light that is scattered, reflected, or refracted from the target; and
    a processor configured to determine a characteristic of the target based on an analysis result of the first image signal and the second image signal.

2. The apparatus of claim 1, wherein a number of the plurality of first image sensors of the first sensor array and a number of the plurality of second image sensors of the second sensor array are predetermined unit numbers.

3. The apparatus of claim 1, wherein the processor is further configured to adjust an operation method of at least one of the light source, the first sensor array, and the second sensor array, according to the analysis result.

4. The apparatus of claim 1, wherein the processor is further configured to control the light source to adjust at least one of an intensity of the light output from the light source and an output angle of the light output from the light source, according to the analysis result.

5. The apparatus of claim 1, wherein the processor is further configured to adjust an exposure time of at least one of the first sensor array and the second sensor array, according to the analysis result.

6. An apparatus for processing an optical signal, the apparatus comprising:
    a light source configured to output a light;
    a first sensor array comprising a plurality of first image sensors configured to obtain a first image signal by detecting the light that is scattered, reflected, or refracted from a target;
    a second sensor array disposed in an area adjacent to the first sensor array, the second sensor array comprising a plurality of second image sensors configured to obtain a second image signal having repeatability with the first image signal by detecting the light that is scattered, reflected, or refracted from the target; and
    a processor configured to determine a characteristic of the target based on a signal to noise ratio (SNR) of the first image signal or the second image signal, and
    wherein the processor is further configured to adjust an operation method of at least one of the light source, the first sensor array, and the second sensor array according to the SNR when the SNR is less than a predetermined value.

7. An apparatus for processing an optical signal, the apparatus comprising:
    a light source configured to output a light;
    a first sensor array comprising a plurality of first image sensors configured to obtain a first image signal by detecting the light that is scattered, reflected, or refracted from a target:
    a second sensor array disposed in an area adjacent to the first sensor array, the second sensor array comprising a plurality of second image sensors configured to obtain a second image signal having repeatability with the first image signal by detecting the light that is scattered, reflected, or refracted from the target; and
    a processor configured to determine a characteristic of the target based on a saturation degree of the first image signal or the second image signal, and
    wherein the processor is further configured to adjust an exposure time of at least one of the first sensor array and the second sensor array according to the saturation degree when the saturation degree is greater than or equal to a predetermined value.

8. The apparatus of claim 1, wherein the processor is further configured to select one of the first image signal and the second image signal based on the analysis result, and determine the characteristic of the target based on the selected one of the first image signal and the second image signal.

9. An apparatus for processing an optical signal, the apparatus comprising:
    a light source configured to output a light;

a first sensor array comprising a plurality of first image sensors configured to obtain a first image signal by detecting the light that is scattered, reflected, or refracted from a target;

a second sensor array disposed in an area adjacent to the first sensor array, the second sensor array comprising a plurality of second image sensors configured to obtain a second image signal having repeatability with the first image signal by detecting the light that is scattered, reflected, or refracted from the target; and a processor configured to obtain an analysis result of the first image signal and the second image signal by comparing the first image signal to the second image signal based on a position of a first reference sensor which is one of the plurality of first image sensors and a position of a second reference sensor which is one of the plurality of second image sensors, and determine a characteristic of the target based on the analysis result of the first image signal and the second image signal.

10. The apparatus of claim 9, wherein the processor is further configured to determine offsets of the first image signal and the second image signal by using a signal obtained from the first reference sensor and a signal obtained from the second reference sensor.

11. A method of processing an optical signal, the method comprising:

outputting a light;

obtaining a first image signal by detecting the light that is scattered, reflected, or refracted from a target by using a first sensor array disposed on a two dimensional surface and comprising a plurality of first image sensors;

obtaining a second image signal having repeatability with the first image signal by detecting the light that is scattered, reflected, or refracted from the target by using a second sensor array that is disposed to share a boundary with the first sensor array on the same two dimensional surface and comprises a plurality of second image sensors; and determining a characteristic of the target based on an analysis result of the first image signal and the second image signal.

12. The method of claim 11, wherein a number of the plurality of first image sensors of the first sensor array and a number of the plurality of second image sensors of the second sensor array are predetermined unit numbers.

13. The method of claim 11, further comprising adjusting at least one of an operation method of outputting the light, an operation method of obtaining the first image signal, and an operation method of obtaining the second image signal, according to the analysis result.

14. The method of claim 11, wherein the method further comprises:

adjusting at least one of an intensity of the outputted light and an output angle of the outputted light according to the analysis result.

15. The method of claim 11, wherein the method further comprises:

adjusting an exposure time of at least one of the first sensor array and the second sensor array, according to the analysis result.

16. A method of processing an optical signal, the method comprising:

outputting a light;

obtaining a first image signal by detecting the light that is scattered, reflected, or refracted from a target by using a first sensor array comprising a plurality of first image sensors;

obtaining a second image signal having repeatability with the first image signal by detecting the light that is scattered, reflected, or refracted from the target by using a second sensor array that is disposed in an area adjacent to the first sensor array and comprises a plurality of second image sensors;

determining a characteristic of the target based on a signal to noise ratio (SNR) of the first image signal or the second image signal; and adjusting at least one of an operation method of outputting the light, an operation method of obtaining the first image signal, and an operation method of obtaining the second image signal, according to the SNR when the SNR is less than a predetermined value.

17. A method of processing an optical signal, the method comprising:

outputting a light;

obtaining a first image signal by detecting the light that is scattered, reflected, or refracted from a target by using a first sensor array comprising a plurality of first image sensors;

obtaining a second image signal having repeatability with the first image signal by detecting the light that is scattered, reflected, or refracted from the target by using a second sensor array that is disposed in an area adjacent to the first sensor array and comprises a plurality of second image sensors;

determining a characteristic of the target based on a saturation degree of the first image signal or the second image signal; and adjusting an exposure time of at least one of the first sensor array and the second sensor array, according to the saturation degree when the saturation degree is greater than or equal to a predetermined value.

18. The method of claim 11, further comprising:

determining the characteristic of the target by using one of the first image signal and the second image signal according to the analysis result.

19. A method of processing an optical signal, the method comprising:

outputting a light;

obtaining a first image signal by detecting the light that is scattered, reflected, or refracted from a target by using a first sensor array comprising a plurality of first image sensors;

obtaining a second image signal having repeatability with the first image signal by detecting the light that is scattered, reflected, or refracted from the target by using a second sensor array that is disposed in an area adjacent to the first sensor array and comprises a plurality of second image sensors;

obtaining an analysis result by comparing the first image signal to the second image signal based on a position of a first reference sensor which is one of the plurality of first image sensors and a position of a second reference sensor which is one of the plurality of second image sensors; and determining a characteristic of the target based on the analysis result of the first image signal and the second image signal.

20. The method of claim 19, further comprising: determining offsets of the first image signal and the second image signal by using a signal obtained from the first reference sensor and a signal obtained from the second reference sensor.

21. A non-transitory computer-readable storage medium storing a program that is executable by a computer to perform the method of claim 11.

* * * * *